United States Patent
Perrelli et al.

(10) Patent No.: US 9,932,217 B2
(45) Date of Patent: Apr. 3, 2018

(54) SYSTEM AND APPARATUS FOR OPTIMIZING HYDRATION AND FOR THE CONTEXTUAL DISPENSING OF ADDITIVES

(71) Applicant: LifeFuels, Inc., Reston, VA (US)

(72) Inventors: Jonathon E. Perrelli, Reston, VA (US); David J. Wheatley, Reston, VA (US); Todd Metlen, Ojai, CA (US); Maxim D. Wheatley, Reston, VA (US); Connor J. Bacon, Reston, VA (US)

(73) Assignee: LifeFuels, Inc., Reston, VA (US)

( * ) Notice: Subject to any disclaimer, the term of this patent is extended or adjusted under 35 U.S.C. 154(b) by 0 days.

(21) Appl. No.: 14/960,109

(22) Filed: Dec. 4, 2015

(65) Prior Publication Data
US 2016/0159632 A1 Jun. 9, 2016

Related U.S. Application Data

(60) Provisional application No. 62/088,189, filed on Dec. 5, 2014, provisional application No. 62/174,415, filed
(Continued)

(51) Int. Cl.
*B67D 1/08* (2006.01)
*B67D 1/00* (2006.01)
(Continued)

(52) U.S. Cl.
CPC ....... *B67D 1/0882* (2013.01); *B65D 47/0857* (2013.01); *B65D 51/2807* (2013.01);
(Continued)

(58) Field of Classification Search
CPC ............. B67D 1/0081; B67D 1/0882; B67D 2001/0093; B67D 1/0015;
(Continued)

(56) References Cited

U.S. PATENT DOCUMENTS

| D97,347 S | 10/1935 | Gambell |
| 2,071,399 A | 2/1937 | Gambell |

(Continued)

FOREIGN PATENT DOCUMENTS

DE 3428178 A1 2/1986

*Primary Examiner* — Michael Collins
(74) *Attorney, Agent, or Firm* — Ked & Associates, LLP

(57) ABSTRACT

Provided are systems, methods, and apparatuses for a portable hydration system including a mechanical or electromechanical mechanism for dispensing additives into a liquid or other solute in a portable container. Such additives include solids, liquid, powders, and gases, and include vitamins, minerals, nutritional supplements, pharmaceuticals, and other consumables. Additives are introduced into the hydration device via closed vessels equipped with RFID tags or similar, capable of transferring data about the vessels' contents to the device. Dispensing is initiated manually by direct user action, automatically by the device, and/or externally through an associated application on a user device. Dispensing is adjustable by contextual factors such as a user's preferences, location, activity, physiologic status, and the like, obtained via APIs to third party applications or through more direct measurements or inputs. Consumption of additives and consumable liquids in the container is measured and monitored, and the data used to generate recommendations.

17 Claims, 19 Drawing Sheets

Related U.S. Application Data on Jun. 11, 2015, provisional application No. 62/174,466, filed on Jun. 11, 2015, provisional application No. 62/174,935, filed on Jun. 12, 2015.

(51) Int. Cl.
  *B65D 47/08* (2006.01)
  *B65D 51/28* (2006.01)
  *G06F 19/00* (2018.01)
  *A45F 3/16* (2006.01)

(52) U.S. Cl.
  CPC ......... *B67D 1/0015* (2013.01); *B67D 1/0081* (2013.01); *G06F 19/3475* (2013.01); *A45F 3/16* (2013.01); *B65D 2543/00046* (2013.01); *B67D 2001/0093* (2013.01); *B67D 2001/0096* (2013.01)

(58) Field of Classification Search
  CPC ........ B67D 2001/0096; B65D 47/0857; B65D 51/2807; B65D 2543/00046; G06F 19/3475; A45F 3/16
  USPC .................................................. 700/231–244
  See application file for complete search history.

(56) References Cited

U.S. PATENT DOCUMENTS

| | | |
|---|---|---|
| D157,486 S | 2/1950 | Glowacki |
| 2,682,355 A | 6/1954 | Robbins |
| D192,814 S | 5/1962 | Edwin |
| 3,319,637 A | 5/1967 | Gore et al. |
| 3,548,657 A | 12/1970 | Panerai et al. |
| D225,364 S | 12/1972 | Antoni |
| 3,727,803 A | 4/1973 | Cobb |
| D242,132 S | 11/1976 | Hasegawa |
| 4,051,726 A | 10/1977 | Hastbacka |
| 4,087,024 A | 5/1978 | Martin et al. |
| 4,125,187 A | 11/1978 | Vecchiotti |
| 4,133,457 A | 1/1979 | Klassen |
| 4,450,722 A | 5/1984 | Keyes, IV et al. |
| D279,621 S | 7/1985 | Richer |
| 4,728,006 A | 3/1988 | Drobish et al. |
| D295,954 S | 5/1988 | Kirchhoff |
| D296,302 S | 6/1988 | Weber |
| 4,898,306 A | 2/1990 | Pardes |
| 5,080,260 A | 1/1992 | Düring |
| 5,119,279 A | 6/1992 | Makowsky |
| 5,139,169 A | 8/1992 | Boyer |
| 5,174,458 A | 12/1992 | Segati |
| D336,216 S | 6/1993 | Rohrbeck |
| 5,325,765 A | 7/1994 | Sylvan |
| D352,204 S | 11/1994 | Hayes |
| 5,377,877 A | 1/1995 | Brown et al. |
| 5,379,916 A | 1/1995 | Martindale |
| 5,398,853 A | 3/1995 | Latham |
| 5,474,211 A | 12/1995 | Hellenberg |
| D372,867 S | 8/1996 | Lambelet |
| D382,808 S | 8/1997 | Fenton |
| D383,383 S | 9/1997 | Prestia |
| D387,992 S | 12/1997 | Kotoucek |
| 5,747,824 A | 5/1998 | Jung et al. |
| D396,603 S | 8/1998 | Gasser |
| 5,938,080 A | 8/1999 | Haaser et al. |
| 6,077,579 A | 6/2000 | De Laforcade |
| 6,142,063 A | 11/2000 | Beaulieu |
| 6,170,712 B1 | 1/2001 | Kasboske |
| 6,230,884 B1 | 5/2001 | Coory |
| 6,422,422 B1 | 7/2002 | Forbes |
| 6,504,481 B2 | 1/2003 | Teller |
| D477,791 S | 7/2003 | Wells |
| D478,073 S | 8/2003 | Topinka |
| 6,615,881 B2 | 9/2003 | Bartholomew et al. |
| 6,644,471 B1 | 11/2003 | Anderson |
| 6,722,530 B1 | 4/2004 | King et al. |
| 6,761,318 B2 | 7/2004 | Dudek et al. |
| D500,936 S | 1/2005 | Nikkhah |
| 6,889,872 B2 | 5/2005 | Herman et al. |
| 6,921,911 B2 | 7/2005 | Siepmann |
| 6,925,871 B2 | 8/2005 | Frank |
| 6,935,493 B2 | 8/2005 | Cho |
| D514,385 S | 2/2006 | Smith |
| D517,852 S | 3/2006 | Jalet |
| D522,860 S | 6/2006 | LaFortune |
| D523,332 S | 6/2006 | McEldowney |
| D525,135 S | 7/2006 | Bakic |
| 7,104,184 B2 | 9/2006 | Biderman et al. |
| 7,107,838 B2 | 9/2006 | Chai et al. |
| D529,340 S | 10/2006 | Laib |
| 7,172,095 B2 | 2/2007 | Marshall |
| 7,196,624 B2 | 3/2007 | Teller |
| D541,596 S | 5/2007 | Hicks |
| 7,228,879 B2 | 6/2007 | Miller et al. |
| 7,319,523 B2 | 1/2008 | Chiarello |
| D565,350 S | 4/2008 | Gauger |
| D572,588 S | 7/2008 | Osborn |
| D573,464 S | 7/2008 | Kogure |
| 7,439,859 B2 | 10/2008 | Humphrey |
| 7,464,811 B2 | 12/2008 | Patterson |
| 7,501,933 B2 | 3/2009 | Rousso et al. |
| D591,599 S | 5/2009 | Okin |
| D593,411 S | 6/2009 | Bizzell |
| 7,614,496 B2 | 11/2009 | Dvorak |
| D608,637 S | 1/2010 | Getsy |
| D611,298 S | 3/2010 | Freeman |
| 7,710,567 B1 | 5/2010 | Mentzer et al. |
| D618,963 S | 7/2010 | Freeman |
| 7,762,181 B2 | 7/2010 | Boland et al. |
| D634,157 S | 3/2011 | Hoff |
| D635,823 S | 4/2011 | Mauffette |
| D635,864 S | 4/2011 | Lee |
| D639,607 S | 6/2011 | Bracq |
| 8,083,055 B2 | 12/2011 | Simonian |
| 8,091,735 B2 | 1/2012 | Girard et al. |
| 8,141,700 B2 | 3/2012 | Simonian |
| D658,982 S | 5/2012 | Pauser |
| D659,472 S | 5/2012 | D'Amato |
| 8,196,776 B2 | 6/2012 | Doglioni Majer |
| 8,210,396 B2 | 7/2012 | Girard et al. |
| 8,240,508 B2 | 8/2012 | Wegelin et al. |
| 8,302,795 B2 | 11/2012 | Van den Broek |
| 8,361,527 B2 | 1/2013 | Winkler |
| 8,378,830 B2 | 2/2013 | Moran |
| 8,397,519 B2 | 3/2013 | Loibl et al. |
| 8,417,377 B2 | 4/2013 | Rothchild |
| 8,464,633 B2 | 6/2013 | Anson |
| 8,485,359 B2 | 7/2013 | Anderson |
| 8,522,968 B2 | 9/2013 | Middleman |
| 8,523,837 B2 | 9/2013 | Wiggins |
| D690,990 S | 10/2013 | Boggs |
| D690,991 S | 10/2013 | Boggs |
| 8,556,127 B2 | 10/2013 | Olson et al. |
| 8,584,691 B2 | 11/2013 | Hammonds |
| 8,584,840 B2 | 11/2013 | Kim |
| 8,590,753 B2 | 11/2013 | Marina et al. |
| D699,106 S | 2/2014 | Glaser |
| D699,996 S | 2/2014 | De Leo |
| 8,678,183 B2 | 3/2014 | Jones |
| 8,684,231 B2 | 4/2014 | Lane |
| 8,695,420 B1 | 4/2014 | Korman et al. |
| 8,701,906 B1 | 4/2014 | Anderson |
| 8,717,182 B1 | 5/2014 | Brashears et al. |
| 8,718,819 B2 | 5/2014 | Hyde et al. |
| 8,754,769 B2 | 6/2014 | Stein et al. |
| 8,757,227 B2 | 6/2014 | Girard et al. |
| 8,794,485 B2 | 8/2014 | Lunn et al. |
| 8,801,688 B2 | 8/2014 | Wiggins |
| 8,940,163 B2 | 1/2015 | Bassett |
| 8,945,374 B2 | 2/2015 | Chase |
| 8,977,389 B2 | 3/2015 | Witchell et al. |
| 8,979,539 B1 | 3/2015 | Snyder |
| 8,985,395 B2 | 3/2015 | Tansey |
| 8,989,673 B2 | 3/2015 | Sandy |

(56) References Cited

U.S. PATENT DOCUMENTS

| | | | |
|---|---|---|---|
| 9,014,846 B2 | 4/2015 | Newman | |
| 9,020,635 B2 | 4/2015 | Hortin | |
| 9,035,222 B2* | 5/2015 | Alexander | 165/58 |
| 9,035,765 B2 | 5/2015 | Engelhard et al. | |
| 9,111,324 B2 | 8/2015 | Hyde et al. | |
| 9,126,738 B2 | 9/2015 | Boggs et al. | |
| 9,134,020 B1 | 9/2015 | Wells | |
| 9,138,091 B2 | 9/2015 | Zhao et al. | |
| 9,151,605 B1 | 10/2015 | Sweeney et al. | |
| 9,161,654 B2 | 10/2015 | Belmont | |
| 9,169,112 B2 | 10/2015 | Chase et al. | |
| D746,046 S | 12/2015 | Lee | |
| D748,955 S | 2/2016 | Oliver | |
| 9,254,250 B1 | 2/2016 | Orofino | |
| D751,865 S | 3/2016 | Harris | |
| D752,396 S | 3/2016 | Tu | |
| D758,868 S | 6/2016 | Bretschneider | |
| D760,537 S | 7/2016 | Hertaus | |
| 9,506,798 B2* | 11/2016 | Saltzgiver | G01F 23/263 |
| 2002/0070861 A1 | 6/2002 | Teller | |
| 2002/0090426 A1 | 7/2002 | Denny | |
| 2002/0129663 A1 | 9/2002 | Hoyt et al. | |
| 2007/0214055 A1 | 9/2007 | Temko | |
| 2009/0120815 A1 | 5/2009 | Mitchell | |
| 2009/0206084 A1* | 8/2009 | Woolf | B65D 81/3205 220/500 |
| 2009/0272274 A1 | 11/2009 | De Graaff et al. | |
| 2010/0055252 A1* | 3/2010 | Marina | A47J 31/407 426/77 |
| 2010/0163567 A1 | 7/2010 | Chiang et al. | |
| 2010/0183776 A1 | 7/2010 | Gruenwald | |
| 2011/0006071 A1 | 1/2011 | Koumans | |
| 2011/0049161 A1 | 3/2011 | Savinsky | |
| 2011/0050431 A1 | 3/2011 | Hood | |
| 2011/0052764 A1 | 3/2011 | Bulgin | |
| 2011/0166910 A1* | 7/2011 | Marina | B65D 51/2807 705/7.29 |
| 2011/0180563 A1* | 7/2011 | Fitchett | B67D 3/0051 222/1 |
| 2012/0017766 A1 | 1/2012 | Anson | |
| 2012/0094261 A1 | 4/2012 | Hayn et al. | |
| 2012/0097567 A1 | 4/2012 | Zhao | |
| 2012/0104023 A1 | 5/2012 | Anselmino et al. | |
| 2012/0173164 A1 | 7/2012 | Steuerwald | |
| 2012/0234183 A1 | 9/2012 | Edwards et al. | |
| 2013/0043304 A1 | 2/2013 | Agon et al. | |
| 2013/0092567 A1 | 4/2013 | Lok | |
| 2013/0127748 A1 | 5/2013 | Vertegaal | |
| 2013/0139703 A1 | 6/2013 | Hogarth | |
| 2013/0156904 A1 | 6/2013 | Nosler | |
| 2013/0186779 A1 | 7/2013 | Kambouris | |
| 2013/0240079 A1 | 9/2013 | Petrini | |
| 2013/0319915 A1 | 12/2013 | Gellibolian | |
| 2014/0110476 A1 | 4/2014 | Sheehan et al. | |
| 2014/0114469 A1 | 4/2014 | Givens et al. | |
| 2014/0273925 A1 | 9/2014 | Burgett et al. | |
| 2014/0277707 A1 | 9/2014 | Akdogan et al. | |
| 2014/0303790 A1 | 10/2014 | Huang et al. | |
| 2014/0305952 A1 | 10/2014 | Harris et al. | |
| 2014/0312247 A1 | 10/2014 | McKee et al. | |
| 2014/0324585 A1 | 10/2014 | Mederos | |
| 2014/0335490 A1 | 11/2014 | Baarman et al. | |
| 2014/0352843 A1 | 12/2014 | Solera et al. | |
| 2014/0354438 A1 | 12/2014 | Hazen et al. | |
| 2014/0372045 A1 | 12/2014 | Keski-Pukkila et al. | |
| 2015/0014369 A1 | 1/2015 | Hatton et al. | |
| 2015/0024349 A1 | 1/2015 | Bischoff et al. | |
| 2015/0088304 A1* | 3/2015 | Ameye | A47J 31/40 700/233 |
| 2015/0115158 A1 | 4/2015 | Fu et al. | |
| 2015/0060482 A1 | 5/2015 | Murray et al. | |
| 2015/0122688 A1 | 5/2015 | Dias et al. | |
| 2015/0173488 A1 | 6/2015 | Witchell et al. | |
| 2015/0175400 A1 | 6/2015 | Newman | |
| 2015/0182797 A1 | 7/2015 | Wernow et al. | |
| 2015/0183627 A1 | 7/2015 | Tansey, Jr. | |
| 2015/0284163 A1 | 10/2015 | Manwani et al. | |
| 2016/0159632 A1* | 6/2016 | Wheatley | G06F 19/3475 222/1 |
| 2016/0174470 A1 | 6/2016 | Shaffer | |
| 2017/0156540 A1 | 6/2017 | Wheatley | |

* cited by examiner

US 9,932,217 B2

SYSTEM AND APPARATUS FOR OPTIMIZING HYDRATION AND FOR THE CONTEXTUAL DISPENSING OF ADDITIVES

The present application claims priority to U.S. Provisional Patent Application Ser. No. 62/088,189, filed Dec. 5, 2014, U.S. Provisional Patent Application Ser. No. 62/174,415, filed Jun. 11, 2015, U.S. Provisional Patent Application Ser. No. 62/174,466, filed Jun. 11, 2015, and U.S. Provisional Patent Application Ser. No. 62/174,935, filed Jun. 12, 2015, the entire disclosures of which are hereby incorporated by reference.

BACKGROUND

Portable refillable bottles and other containers used for water and other beverages are widely used and are important for health and hydration. However, one limitation of such bottles and containers is that the consumable contents remain constant and unchanged except for changes in quantity as the contents (frequently, but not exclusively water) are consumed and replenished. Furthermore, vitamins, health, and dietary supplements in the form of liquids, powders, gels, and solid tablets are becoming increasingly popular and more widely consumed. In addition, such supplements and additives are frequently being supplied in bulk to the consumer since they are using and consuming such supplements and additives regularly and on a long term basis.

SUMMARY

This Summary introduces a selection of concepts in a simplified form in order to provide a basic understanding of some aspects of the present disclosure. This Summary is not an extensive overview of the disclosure, and is not intended to identify key or critical elements of the disclosure or to delineate the scope of the disclosure. This Summary merely presents some of the concepts of the disclosure as a prelude to the Detailed Description provided below.

The present disclosure generally relates to hydration systems, methods, and apparatuses. More specifically, aspects of the present disclosure relate to a portable hydration system that includes a mechanical or electromechanical mechanism for periodically dispensing additives into a liquid or other solute in a portable container.

One embodiment of the present disclosure relates to a portable container for retaining a consumable liquid, the container comprising: at least one aperture that receives a vessel containing an additive to be dispensed into the consumable liquid; and a dispensing assembly that dispenses variable quantities of an additive contained in a vessel received in the at least one aperture based on data associated with use of the portable container by a user.

In another embodiment, the portable container includes at least one processor configured to adaptively control the dispensing assembly to dispense the variable quantities of the additive based on the data associated with use of the portable container by a user.

In another embodiment, the at least one processor of the portable container is configured to: control timing of dispensing of the additive from the vessel into the consumable liquid; control an amount of pressure applied to the vessel by the dispensing assembly; and control duration of the application of pressure.

In another embodiment, the at least one processor of the portable container is configured to collect data associated with use of the portable container, and adjust the dispensing of the additive based on the collected data, where the collected data includes one or more of the following: an amount of the consumable liquid retained in the container; a physical characteristic of the additive to be dispensed; a consumption activity associated with the user of the container; a preference of the user of the container; and a context of use of the container by the user.

In yet another embodiment, the at least one processor of the portable container is configured to transmit the collected data from the container to a remote server in communication with the container via a communications network, to a user device associated with the user of the container, or both.

In still another embodiment, the at least one processor of the portable container is configured to: receive at the container from the server, from the user device, or from both the server and user device, one or more recommendations for the user of the container, wherein the one or more recommendations are based on the collected data transmitted from the container; and provide the one or more recommendations to the user of the container.

In another embodiment, the portable container further comprises a pressure applicator within the dispensing assembly, where the pressure applicator is moveable into a position proximal or adjacent to a surface of a vessel received in the at least one aperture, and where the pressure applicator is configured to apply pressure to the surface of the vessel to fully or partially release the additive contained in the vessel.

In still another embodiment, the at least one processor of the portable container is configured to: monitor an amount of the consumable liquid retained in the container; determine a type of the consumable liquid retained in the container; monitor a rate of consumption of the consumable liquid retained in the container; and detect when the amount of the consumable liquid retained in the container has increased or decreased.

In yet another embodiment, the at least one processor of the portable container is configured to: process sensor data about the amount, type, and/or rate of consumption of the consumable liquid retained in the container; store the sensor data about the amount, type, and/or rate of consumption of the consumable liquid retained in the container; communicate the sensor data about the amount, type, and/or rate of consumption of the consumable liquid retained in the container over a communication network; and receive data indicating a recommended amount, a recommended type, and/or a recommended rate of consumption of the consumable liquid retained in the container.

In still another embodiment, the at least one processor of the portable container is configured to present, to the user of the container, the received data indicating the recommended amount, the recommended type, and/or the recommended rate of consumption of the consumable liquid retained in the container.

In another embodiment, a vessel received in the at least one aperture of the portable container includes: a form factor enabling the vessel to recover shape after a dispensing event; a dispensing valve permitting the dispensing of variable quantities of the additive contained in the vessel into the consumable liquid; and a valve mechanism enabling the vessel to be removed from the dispensing assembly and stored, replaced, or transferred to a second dispensing assembly.

Another embodiment of the present disclosure relates to a portable dispensing system comprising: a container for retaining a consumable liquid; a vessel containing an additive to be dispensed into the consumable liquid retained in the container; and a dispensing assembly that dispenses variable quantities of the additive contained in the vessel, and adaptively adjusts a quantity of the dispensed additive to achieve a targeted concentration of the additive in the consumable liquid.

In another embodiment, the dispensing assembly of the portable dispensing system is configured to read the data storage tag affixed to the vessel, and control the dispensing of the additive contained in the vessel based on the data stored in the tag.

In another embodiment, the portable dispensing system further comprises at least one processor configured to obtain the data stored in the data storage tag affixed to the vessel, and generate one or more recommendations for a user of the container.

In still another embodiment, the dispensing assembly of the portable dispensing system adjusts the quantity of the dispensed additive based on a level of the consumable liquid retained in the container, and a recommended level of concentration of the additive in the consumable liquid, where the recommended level of concentration of the additive is based on data associated with use of the portable container by a user.

Yet another embodiment of the present disclosure relates to a method comprising: receiving a vessel containing an additive to be dispensed into a consumable liquid retained in a portable container; obtaining data associated with use of the portable container by a user; and dispensing a quantity of the additive contained in the vessel into the consumable liquid retained in the container based on the obtained data associated with use of the portable container by the user.

In another embodiment, the method further comprises: receiving one or more recommendations generated for the user of the container, and adjusting the dispensing of the additive based on the one or more received recommendations, where the one or more recommendations are generated for the user based on one or more of the following: an amount of the consumable liquid retained in the container; a physical characteristic of the additive being dispensed; rate of consumption of the consumable liquid retained in the container; a preference of the user of the container; and a context of use of the container by the user.

In one or more other embodiments, the methods, systems, and apparatuses described herein may optionally include one or more of the following additional features: the one or more recommendations provided to the user include a recommendation about one or more additives to be purchased for future dispensing by the container; the recommendation about one or more additives to be purchased for future dispensing is based on one or more of the following: quantities and dates of previous additive purchases by the user, rate of dispensing of additives into the container of the user, and rate of consumption of the liquid consumable retained in the container of the user; and/or the vessel containing an additive includes a passive data storage tag affixed thereto, the data storage tag storing data associated with the additive contained in the vessel.

Embodiments of some or all of the systems and apparatuses disclosed herein may also be configured to perform some or all of the methods described above and in greater detail below. Embodiments of some or all of the methods disclosed herein may also be represented as instructions embodied on transitory or non-transitory processor-readable storage media such as optical or magnetic memory or represented as a propagated signal provided to a processor or data processing device via a communication network such as, for example, an Internet or telephone connection.

Further scope of applicability of the systems, apparatuses, and methods of the present disclosure will become apparent from the Detailed Description given below. However, it should be understood that the Detailed Description and specific examples, while indicating embodiments of the systems, apparatuses, and methods, are given by way of illustration only, since various changes and modifications within the spirit and scope of the concepts disclosed herein will become apparent to those skilled in the art from this Detailed Description.

BRIEF DESCRIPTION OF DRAWINGS

These and other objects, features, advantages, and characteristics of the present disclosure will become more apparent to those skilled in the art upon consideration of the following Detailed Description, taken in conjunction with the accompanying claims and drawings, all of which form a part of the present disclosure. In the drawings:

Figure 1:
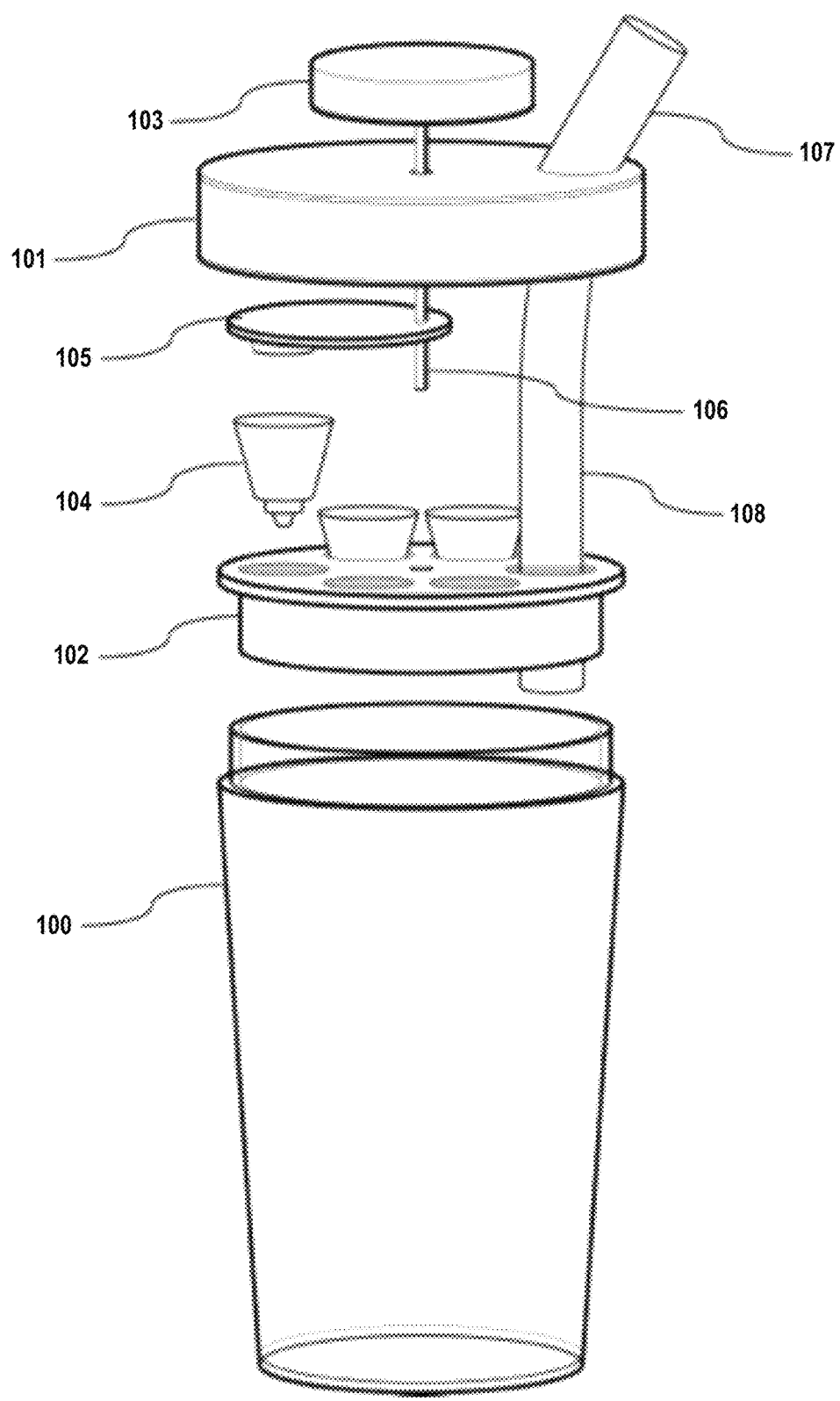
FIG. 1 is a block diagram illustrating an example hydration apparatus in accordance with one or more embodiments described herein.

The headings provided herein are for convenience only and do not necessarily affect the scope or meaning of what is claimed in the present disclosure.

In the drawings, the same reference numerals and any acronyms identify elements or acts with the same or similar structure or functionality for ease of understanding and convenience. The drawings will be described in detail in the course of the following Detailed Description.

DETAILED DESCRIPTION

Various examples and embodiments will now be described. The following description provides specific details for a thorough understanding and enabling description of these examples. One skilled in the relevant art will understand, however, that one or more embodiments described herein may be practiced without many of these details. Likewise, one skilled in the relevant art will also understand that one or more embodiments of the present disclosure can include many other obvious features not described in detail herein. Additionally, some well-known structures or functions may not be shown or described in detail below, so as to avoid unnecessarily obscuring the relevant description.

In view of the above, it is therefore desirable to provide a system and apparatus for combining a user's hydration and additive intake. Such a system and apparatus may, for example, automatically schedule, control, and personalize the user's hydration and additive intake, and may also adjust hydration and additive intake according to the user's environment and/or according to other contextual aspects associated with the user.

Embodiments of the present disclosure relate to a hydration and dispensing system comprising an apparatus including a mechanical/electromechanical dispensing mechanism, that may interface with external, separate wired and/or wireless systems and which dispenses one or more additives into a consumable (e.g., within a container) in a contextually relevant, personalized, and optimized manner. For example, the hydration and dispensing system of the present disclosure may include a hydration device (e.g., a water bottle, container, or the like) that includes one or more discrete apertures or chambers that might contain an additive in solid, liquid, powder, and/or gaseous form, and/or the device or container might receive vessels that interface with the aforementioned apertures or chambers, wherein the vessels contain a solid, liquid, powder, and/or gaseous additive. In accordance with at least one embodiment described herein, the hydration and dispensing system may communicate with one or more integrated or separate processing devices that provide data to further inform, modify, or adjust the dispensing of additives from the aforementioned vessels into the contents of the container. Such data may include, for example, direct user input to prompt a dispensing action, Application Programming Interface (API) data, and/or other information or data to optimize the dispensing based upon relevant environmental, user, and/or other contextual factors including, for example, data or information obtained from wearable fitness devices, mobile devices, the "cloud," and/or other devices or sensors.

Some non-limiting examples of relevant factors that may be used for optimizing the dispensing of additives (where the optimization is with regard to physiological optimization, geographic optimization and/or user preference optimization) include a determined physical location of the user (e.g., based on GPS/location data associated with a mobile device of the user and/or associated with the hydration apparatus of the present disclosure), which may additionally incorporate tagged attributes. For example, geolocation coordinates may be associated with a description or category of the user's physical location and/or additive dispensing requirements (e.g., a geolocation identified as a fitness center has greater hydration requirements, a geolocation identified as a library has greater nootropics, etc.). Weather and other environmental data may be accessed to determine the user's ambient environmental conditions, as well as data indicative of the user's physiological state, physical location, current or recent activity levels, movement, speed of motion, dietary intake, and the like.

The hydration and dispensing systems and apparatuses described herein may dispense additives into the contents of a container, from one or more additive vessels each containing a solid, liquid, powder, and/or gas. The hydration device may dispense such additives either from a distinct and separable additive vessel interfacing with the device, or directly from a chamber within the hydration device itself. The system may operate for single vessel deployments, single additives not contained within an additive vessel, multiple vessel deployments, or any combination thereof. The additives contained in the discrete additive vessels may be dispensed by a dispensing mechanism (described in greater detail below) into a consumable within the container of the system such that any portion of, or the total contents of an additive vessel may be dispensed in a single dispensing event.

It should be noted that, in accordance with at least one embodiment of the present disclosure, the contents of the bottle or container may also be a gas (e.g., pressurized gas). For example, an additive vessel may contain an additive in a liquid, vapor, or gaseous form that is dispensed (e.g., by the dispensing system/mechanism described herein) from the additive vessel into a physically connected container (e.g., bottle, chamber, etc.) containing a pure gas medium (e.g., oxygen).

In accordance with one or more embodiments described herein, the hydration and dispensing system may also incorporate a system leveraging onboard processing, software, secondary device, and/or third party APIs to adjust or otherwise modify the amount and/or concentration of additives dispensed. This additive dispensing may occur in an automated manner according to passive data input and/or in a manual manner according to direct or indirect user input. The automated data input may include, for example, data from a variety of sources including, but not limited to, API feeds, sensor data, and the like. Manual data input may comprise direct or indirect user input that might include specific requests or instructions as well as information such as, for example, food consumption, location, physical activity, as well as more subjective parameters such as tiredness, "overall feeling," and the like.

It should also be noted that in the context of the present disclosure, additives may include, but are not limited to, vitamins, minerals, nutritional and dietary supplements, drugs and pharmaceuticals, herbs, flavorings, colorings, remedies, and other consumables such as coffee, tea, caffeine, and the like.

As will be described in greater detail below, in accordance with at least one embodiment of the present disclosure, the dispensing system may include a solenoid actuator (or other magnetic, hydraulic, or pressure-inducing apparatus) that revolves around a fixed axis to selectively dispense the contents (e.g., additives) from one or more additive vessels/chambers into a receiving area (container) of a hydration device (e.g., a water bottle). For example, the dispensing system is ordinarily in communication with (e.g., has a direct or indirect connection to) water or another solution or medium, enabling the direct or indirect dispensing of the contents of the discrete chambers or additive vessels to mix the additives and solute or medium. The dispensing system may use any of a variety of suitable connections to the solution it deploys additives into, including, for example, a connection via a threaded top for a bottle, a connection through a dispensing nozzle that is held over a container of water, and the like.

FIG. 1 shows an example of a hydration container in accordance with one or more embodiments of the present disclosure. For example, the hydration container 100 may comprise a dispensing module (or dispensing assembly) 102 into which one or more additive vessels 104 may be inserted and enclosed by a lid 101. The module 102 having an aperture through which a drinking channel 107 may pass in order that a user may consume the contents of the container 100. A user may select one of the additive vessels 104 manually by rotating a knob 103 around a central pivot 106 until the pressure actuator 105 is aligned with the desired additive vessel and by applying downward pressure on the knob 103 causing the pressure actuator to apply downward pressure on the additive vessel and thereby dispensing a portion of the additive into the contents of the container 100.

Figure 5A:
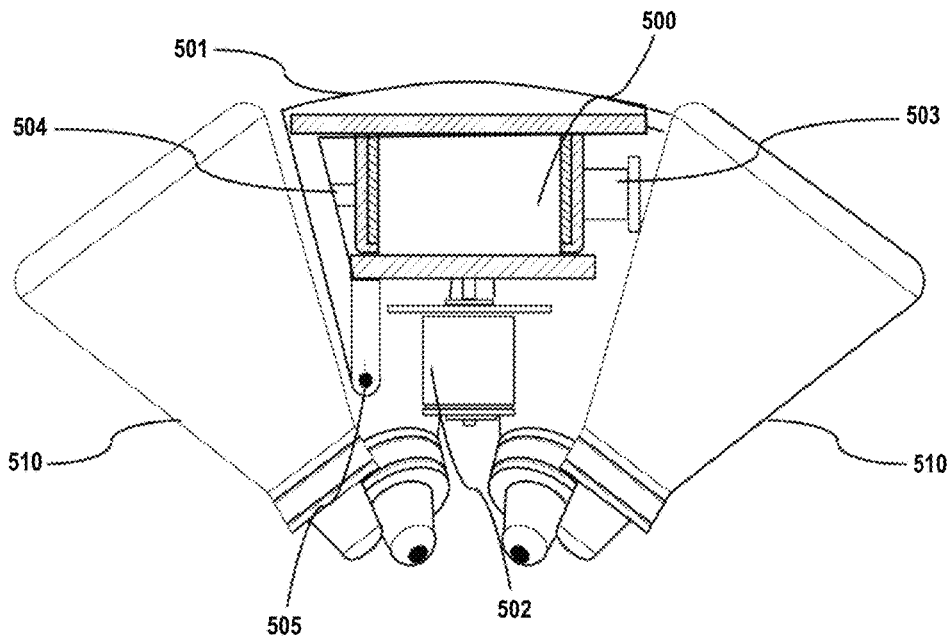
FIG. 5A is a cross-sectional side elevation view of a portion of an example apparatus for dispensing additives into the contents of a container in a first position in accordance with one or more embodiments described herein.
Figure 5B:
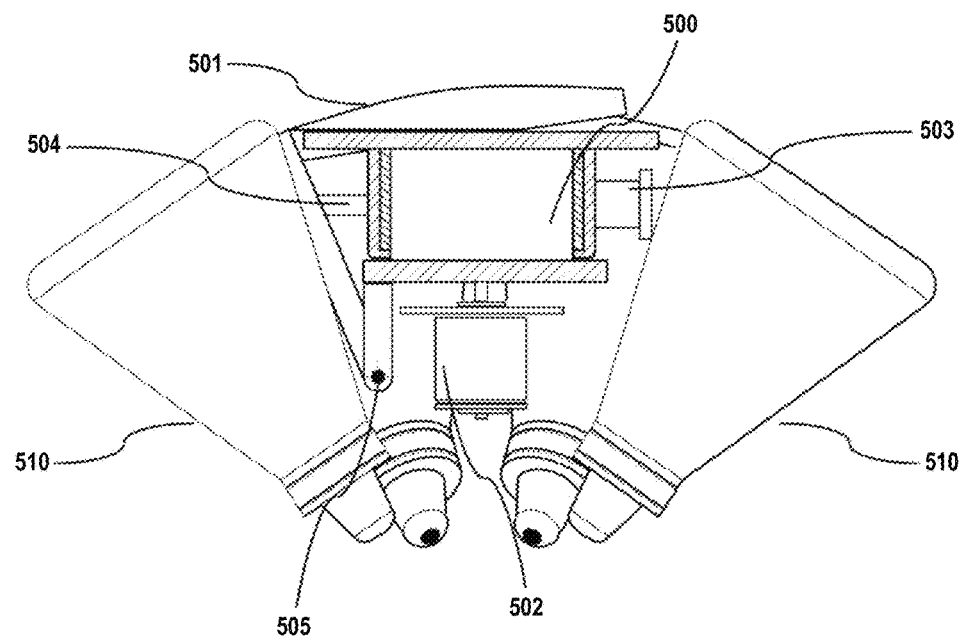
FIG. 5B is a cross-sectional side elevation view of the portion of the example apparatus for dispensing additives into the contents of a container shown in FIG. 5A in a second position in accordance with one or more embodiments described herein.

In accordance with one or more other embodiments, the dispensing module 102 mounted within the hydration container 100 may consist of an electro-mechanical actuator system comprising of a centralized motor, revolving axially to align the pressure actuator with a specific additive vessel (e.g., a vessel containing an additive, which is described in greater detail below) as shown in FIGS. 5A and 5B, and described in further detail below.

The bottle or container may comprise multiple components, some of which may contain electronic and/or mechanical components which are susceptible to damage from water and/or high temperatures and others which come into contact with consumables and which require to be periodically washed. For this reason the hydration system is structured so as to enable the separation of washable from non-washable components or modules.

Figure 2:
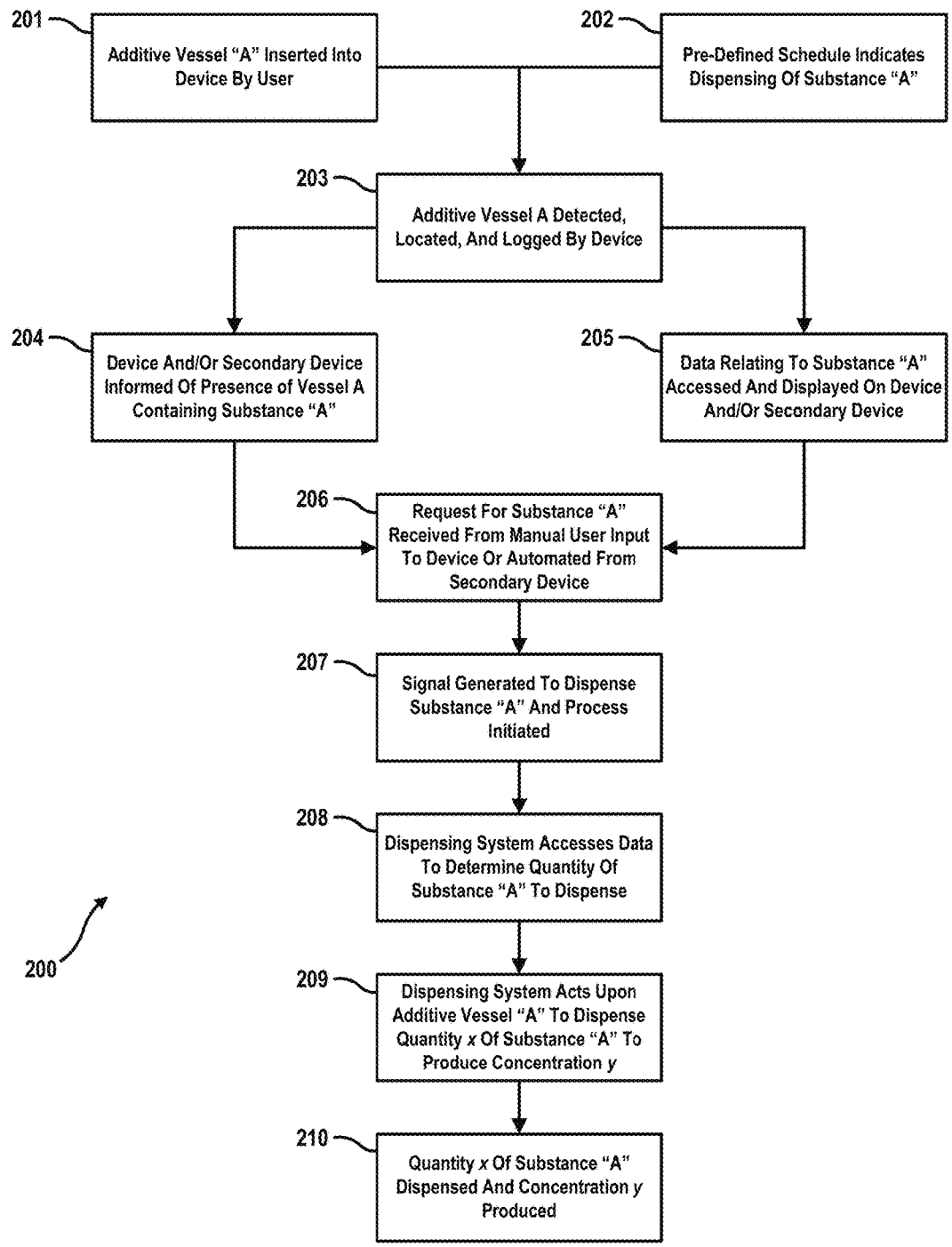
FIG. 2 is a flowchart illustrating an example method for dispensing additives into the contents of a container in accordance with one or more embodiments described herein.

FIG. 2 illustrates an example process 200 for dispensing additives into the contents of a container, in accordance with one or more embodiments described herein. At block 201, a user may insert one or more additive vessels into the hydration container which are then located, identified and the data logged and stored by the hydration device and/or associated secondary device at step 203. An RFID (Radio Frequency Identifications) system, NFC (Near Field Communications) system or other mechanical, electrical, or electronic system capable of detecting the presence of, and identity of containers, informs the device and/or other connected devices that containers/chambers A, B, C, D, E, and F have been loaded with additive vessels.

For example, such identification and data communication may comprise a subsystem whereby each of the additive vessels has a passive RFID or similar type tag attached to an outer wall of the vessel, oriented toward the central axis of the consumable container. An RFID antenna may be mounted on the surface of a rotatable dispensing module located on the central axis of the consumable container and, when closely aligned to an additive vessel, accesses data about the contents of the additive vessel from the RFID tag.

In accordance with one or more embodiments of the present disclosure, the RFID or similar type tag may contain information about the contents of the additive vessel to which it is attached, including, for example, a name or type of additive in the vessel (e.g., vitamin B, cherry flavor, etc.), a category of the additive (e.g., nutritional supplement, pharmaceutical, etc.), a supplier of the additive (e.g., ABC Corp. caffeine), a capacity of the vessel (e.g., 75 drops, 1.5 oz., etc.), a standard serving amount for the particular additive or the particular hydration container (e.g., 3 drops), dosage or consumption limitations for the additive (e.g., 12 drops per day, 4 drops per hour, etc.), as well as various other information that may be pertinent to the contents of the vessel and/or the dispensing of the contents. Data may also include the amount of additive remaining in the vessel and/or the amount dispensed within a previous time period.

In accordance with at least one embodiment, data regarding the dispensing of additives may be encoded in any form suitable or appropriate to the dispensing process. For example, the data may be encoded as a voltage or distance corresponding to the motion required of the rotatable dispensing module and/or pressure actuator. This data is communicated at step 204 to an onboard processor within the hydration container and/or to an associated mobile device. Some or all of the data may also be displayed on an interface screen integrated as part of the hydration device and/or on the display of a secondary device at step 205.

In accordance with one or more embodiments of the present disclosure, data may also be written to the RFID or similar type tag on an additive vessel by one or more processors (e.g., processing chips, processing devices, etc.) within the hydration device. A portion of the contents of an additive vessel may be released into a first container and the additive vessel subsequently transferred by the user to a second container. It is therefore useful to encode data on the vessel's RFID tag including, but not limited to, the quantity of additive remaining in the vessel, the identity of the hydration device in which the vessel was previously used, and/or the identity of the user associated with that previously used hydration device.

At step 202 an additive dispensing schedule requests the dispensing of additive or substance "A", alternatively this may be manually requested by the user or received from a secondary device at step 206, the processor then generates a signal at step 207 to dispense additive "A" from the appropriate additive vessel. The processor may additionally at step 208 adjust the amount of additive dispensed based on other stored data including, but not limited to any determined user preferences (e.g., user prefers stronger concentration) in which case an increased amount of additive may be dispensed. The dispensing module then applies an appropriate input force (e.g., a measured amount of pressure) to the additive vessel at step 209 to dispense a quantity "x" of additive "A".

In accordance with one or more other embodiments of the present disclosure, the system may also have access to sensor data about the volume of water (or other solute) within the hydration container, and may use this sensor data as a further data point at step 210 in order to, for example, adjust the quantity "x" of additive "A" to achieve a specific level of concentration of "y".

Figure 3:
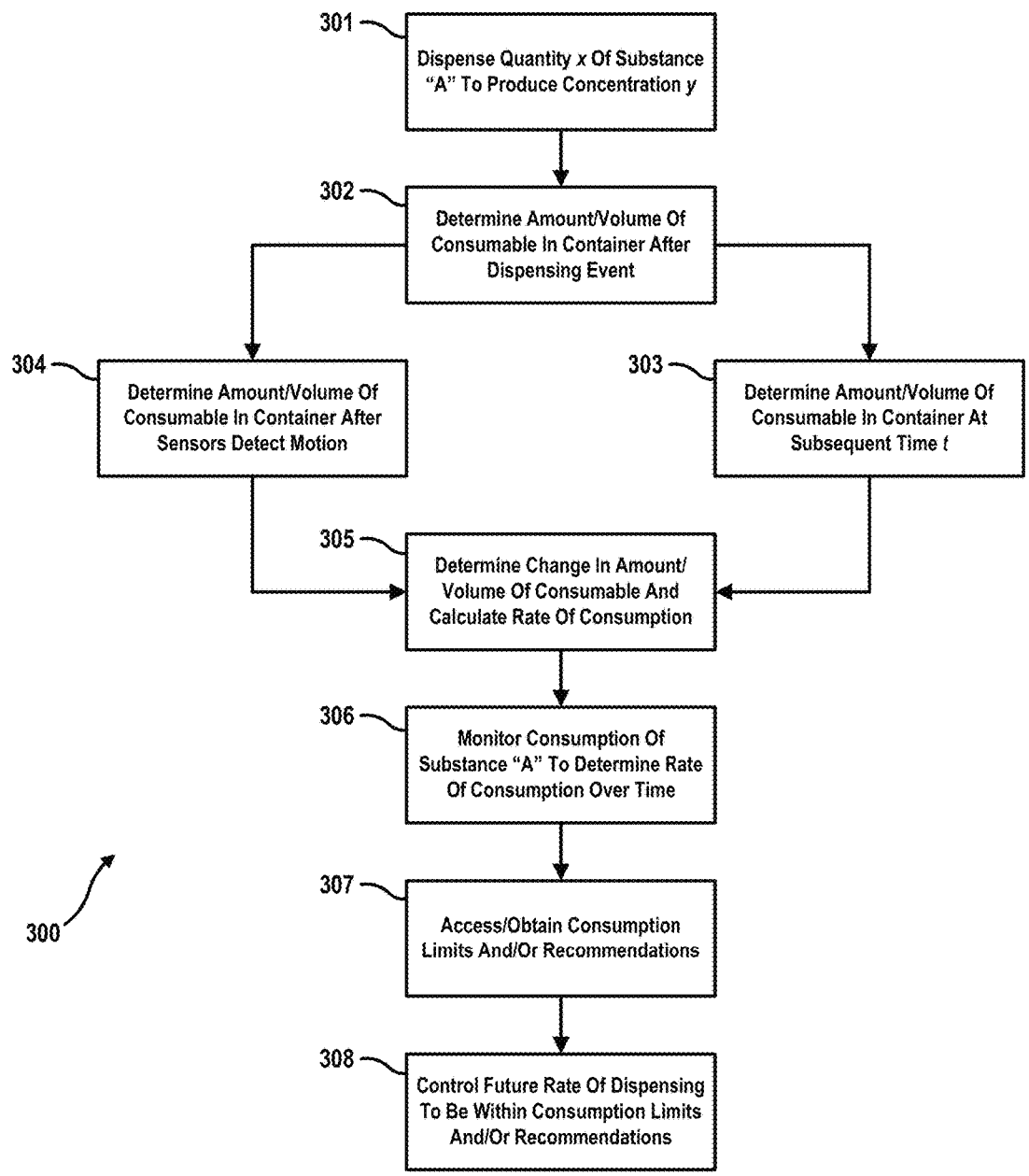
FIG. 3 is a flowchart illustrating an example method for monitoring the consumption of additives and container contents in accordance with one or more embodiments described herein.

FIG. 3 illustrates an example process 300 for monitoring the consumption of additives and container contents in accordance with one or more embodiments described herein. For example, in accordance with at least one embodiment, sensor data about the level or volume of consumable within the container may be used to monitor and control the concentration of additives in order to maintain appropriate consumption limits. Sensors may include IR (Infra-red) LEDs and/or other means of measuring the level of liquid in a container.

At step 301 a quantity "x" of additive "A" is dispensed into a consumable in the hydration container and the amount of consumable is measured immediately after the dispensing event using an array of IR emitters and receivers or by other methods at step 302. The amount of consumable is measured periodically thereafter, this may be at pre-determined time intervals (step 303) and/or may be triggered by sensors which detect a change in level or movement of the hydration container, such as tilting of the container to drink from it (step 304). From this data, the change in volume of consumable can be determined at 305 and a consumption rate over time for additive "A" can be determined at step 306. An onboard or separate processor may then access data on recommended consumption limits for additive "A" at step 307 and may decrease the amount subsequently dispensed at step 308 in the event that the user is consuming the additive at a rate that is greater than the recommended rate.

In addition to the above, sensors may measure the depth or volume of liquid in the container prior to (e.g., immediately prior to) a scheduled dispensing event, and adjust the amount dispensed in order to achieve a specific level of concentration of the additive in the liquid. For example, if the liquid level is determined to be low, less additive may be dispensed. In another example, if the liquid level is determined to be very low, zero, or below a predefined threshold level, the dispensing event may be cancelled altogether and the user alerted accordingly.

Figure 4:
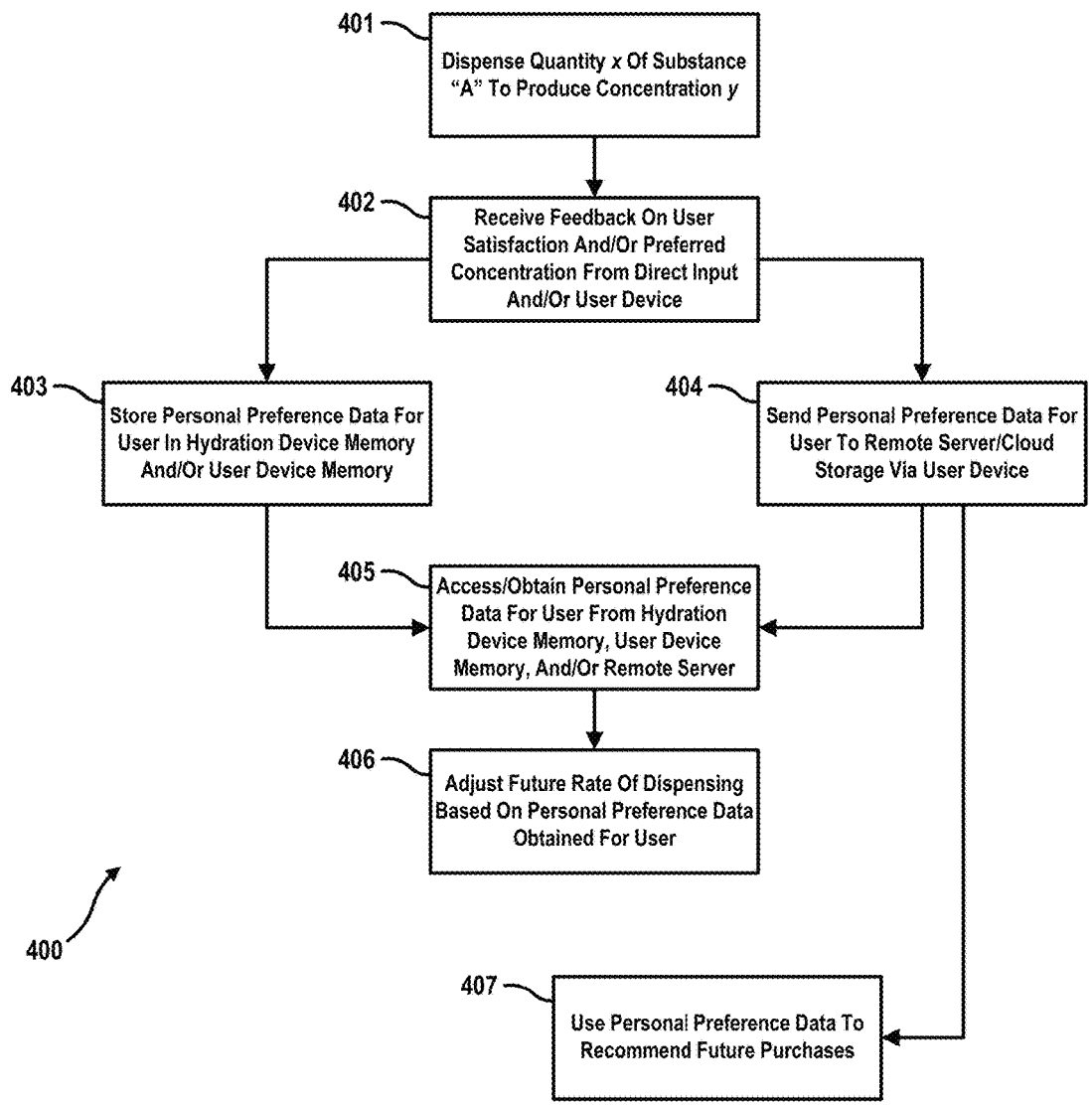
FIG. 4 is a flowchart illustrating an example method for adjusting the dispensing of additives into the contents of a container based on user preferences in accordance with one or more embodiments described herein.

As well as adjusting additive dispensing to remain within maximum or recommended limits, the hydration system may also adjust quantities according to individual user preferences. This may be done automatically or may be based on explicit user feedback. For example, FIG. 4 shows an example process 400 for adjusting the dispensing of additives into the contents of a container in response to explicit user feedback, in accordance with one or more embodiments described herein. At step 401, a quantity of additive is dispensed into the container and at step 402 the user provides feedback on the level of concentration, either directly via a user interface on the hydration container or by using the interface on an associated mobile device, providing feedback to an application residing on the mobile device. The user preference data may be stored locally in the hydration device, locally on the mobile device and/or remotely in the cloud from where it may be accessed by the mobile device and/or the hydration container at step 405. Subsequent dispensing events may then be adjusted based on this user preference data at step 406.

As shown in FIGS. 5A and 5B, the dispensing module 500 may be centrally located on the center-line of the container and equidistant from the additive vessels 510, rotating axially around the center-line to provide targeted compression on an additive vessel 510. A user input and/or an automated signal from an associated mobile device or other external source may be received which specifies the degree of rotation required of the dispensing module 500 in order for an actuator 501 to be aligned with the required additive vessel 510. Rotation of the dispensing module is controlled by an axially positioned stepper motor 502 and may rotate clockwise, counterclockwise or a combination of both in order to position the actuator. The received signal may also specify the stroke-length and/or pressure which should be applied to the additive vessel by the electromagnetic solenoid actuator 501 in order to release the required number of drops or volume of additive. In addition, the signal may also specify a duration and/or frequency with which the pressure is required to be applied to release the required number of drops or volume of additive. The resultant action is the release or dispensing of a specific drop size and/or number of drops from a specific additive vessel as specified by the device's embedded systems and/or from user input (e.g., input received directly via a user interface on the container and/or input received via an associated user device such as, for example, a user's mobile device).

In accordance with one or more embodiments, the dispensing module 500 may also include a stepper motor 502 or similar rotating mechanism to orient the dispensing system. The stepper motor 502 may be informed by onboard software, an onboard processor and/or by a secondary associated device, to rotate the dispensing assembly 500 in order to act upon a specific additive vessel 510, programmatically orienting itself to a set location/interval.

A system of sensors within the dispensing module identifies which additive vessels 510 are loaded and present in the container, the additive or other contents of those vessels, the total amount or capacity of additive or other contents of those vessels, the amount of additive currently remaining within each vessel and the standard or recommended rate of dispensing of that additive and other relevant data. This data is communicated to a processor within the hydration device and subsequently communicated to any other associated software or device with which the hydration device is in communication in order to control the dispensing events.

The pressure actuator 501 rotates from a non-pressure applying position as illustrated in FIG. 5A to a pressure applying position as illustrated in FIG. 5B, to apply direct pressure on the additive vessel 510, thereby causing the expulsion of the contents of the additive vessel 510 in a controlled fashion.

A hinge point assembly 505 for the lever 501 positions all of the apparatus consistently, and protects it from external forces that might cause a misalignment. Conversely, in accordance with at least one embodiment, the non-acting end of the piston of the solenoid actuator 503 may extend beyond a minimum length and locate within a recess in order to create a passive anchoring system, causing the entire dispensing mechanism to "lock" into place at the non-acting end thereby helping ensure that the "acting", pressure applying end of the actuator is properly aligned with the additive vessel and thereby mitigating risk of the system losing alignment.

Figure 6A:
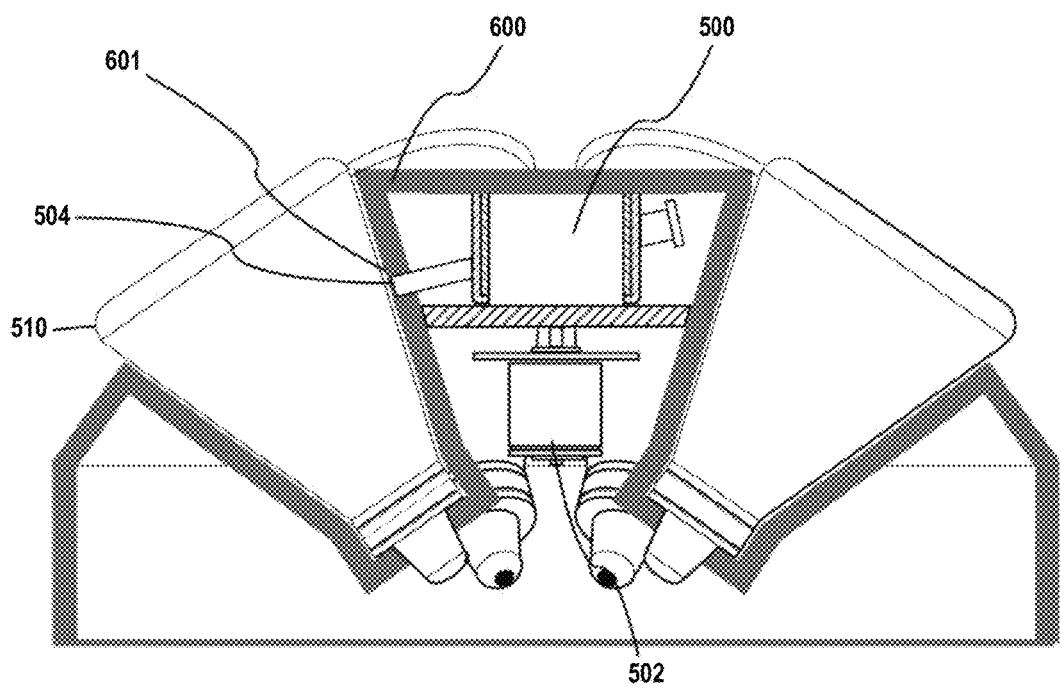
FIG. 6A is a cross-sectional side elevation view of a portion of an example apparatus for dispensing a controlled amount of an additive into the contents of a container in accordance with one or more embodiments described herein.
Figure 6B:
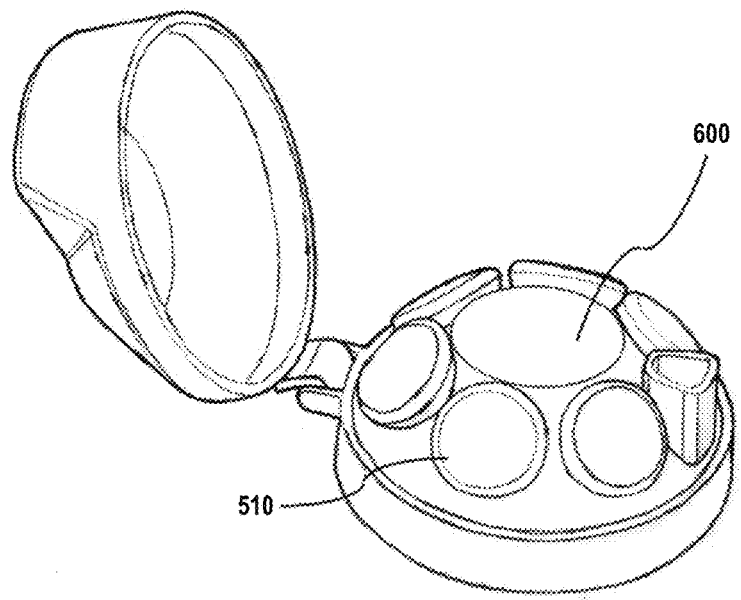
FIG. 6B is a top perspective view of a portion of an example apparatus for dispensing a controlled amount of an additive into the contents of a container in accordance with one or more embodiments described herein.

FIGS. 6A and 6B show different views of a portion of an example apparatus for dispensing a controlled amount of an additive into the contents of a container, in accordance with one or more embodiments of the present disclosure. As shown, the dispensing module assembly may comprise of a complete "wrap-around" housing 600 for the additive vessels 510 in order to ensure that all of the compressing force acts directly upon the contents of the additive vessel 510. The dispensing module 500 may be located in a top portion of a hydration device (e.g., a water bottle or other portable hydration device/system), with the pressure actuator 504 mounted at an angle such that it applies pressure at approximately right angles to the wall of the additive vessel 510. The pressure actuator 504 being rotated by the stepper motor 502 to align with the selected additive vessel 510. The dispensing module 500 may be located in the upper portion of a hydration device or bottle (e.g., hydration device 100 in the example shown in FIG. 1), thereby maximally leveraging the effect of gravity to assist in dispensing the additives.

In accordance with at least one embodiment, the removable additive vessel 510 may also comprise of a compressible, compliant sub-area 601 of the sidewall which is more compressible and compliant than the rest of the vessel walls and which is acted upon by the pressure actuator or piston 504 to pressurize the additive contents for expulsion from a "pore-valve" type mechanism at the base of the vessel 510. Furthermore, in accordance with one or more embodiments, the additive vessel 510 may include a plurality of ribs (e.g., extending along the vessel's side walls) and/or other features to facilitate a reliable and repeatable compression of the vessel.

Figure 7:
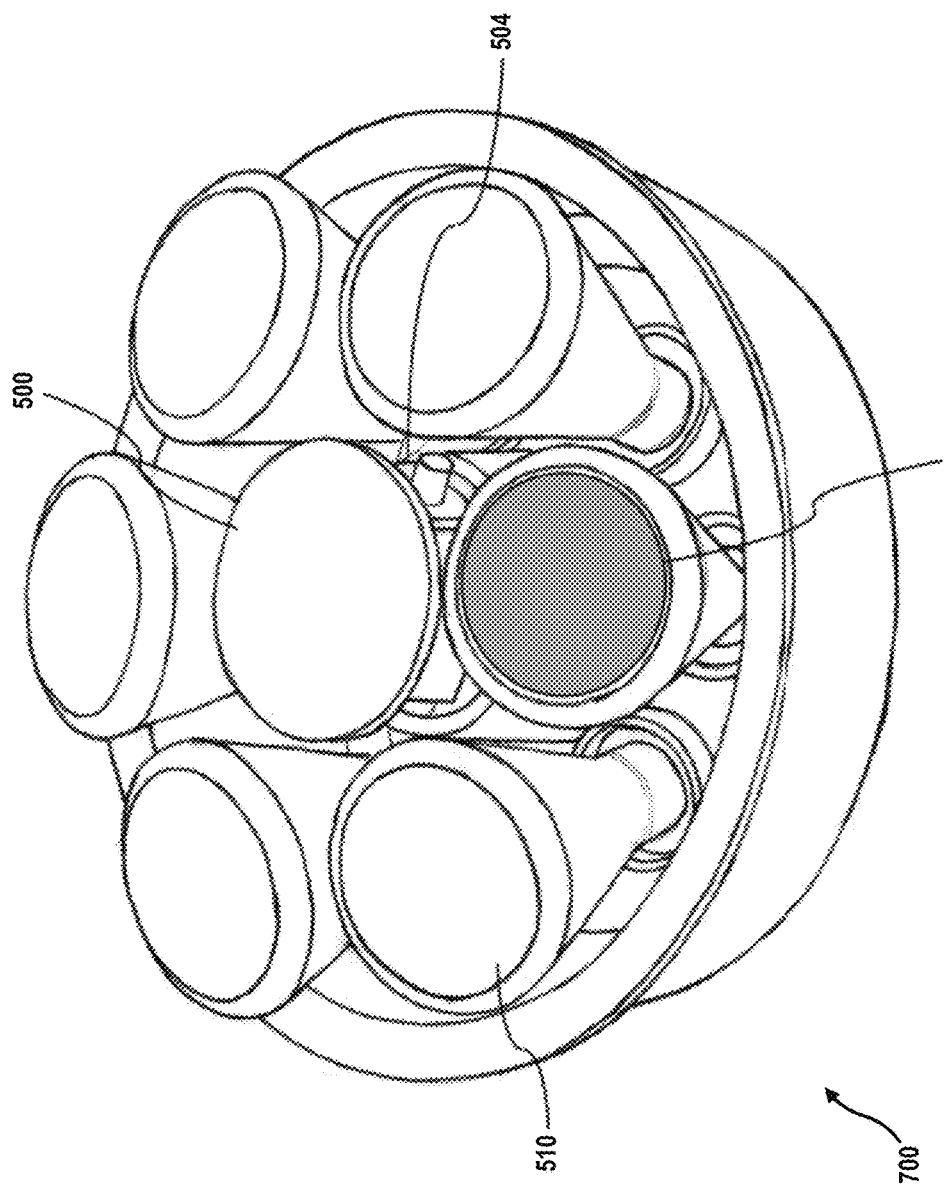
FIG. 7 is a top perspective view of a portion of another example apparatus for dispensing a controlled amount of an additive into the contents of a container in accordance with one or more embodiments described herein.

FIG. 7 shows an example dispensing assembly 700 in accordance with one or more embodiments described herein. The dispensing assembly 700 may include, for example, six additive vessels 510 arranged circumferentially around a central dispensing module 500, whereby the additive vessels 510 are held in place by the lower dispensing nozzle and are additionally oriented close to or equal to, a vertical position in order to maximally leverage gravity in assisting the release of additives from the vessels 510 when pressure is applied by a pressure actuator or piston 504 to the inner walls of the vessels 510. The orientation of additive vessels 510 as illustrated in FIGS. 6B and 7 additionally provides for high brand-visibility for the manufacturers or suppliers of the additive vessels 510 by positioning the larger surface 701 uppermost for labeling purposes. A top cover of the hydration device or container (not shown) may be manufactured from a transparent material in order that the branding or labeling on the top surface of the additive vessels is visible.

Figure 8:
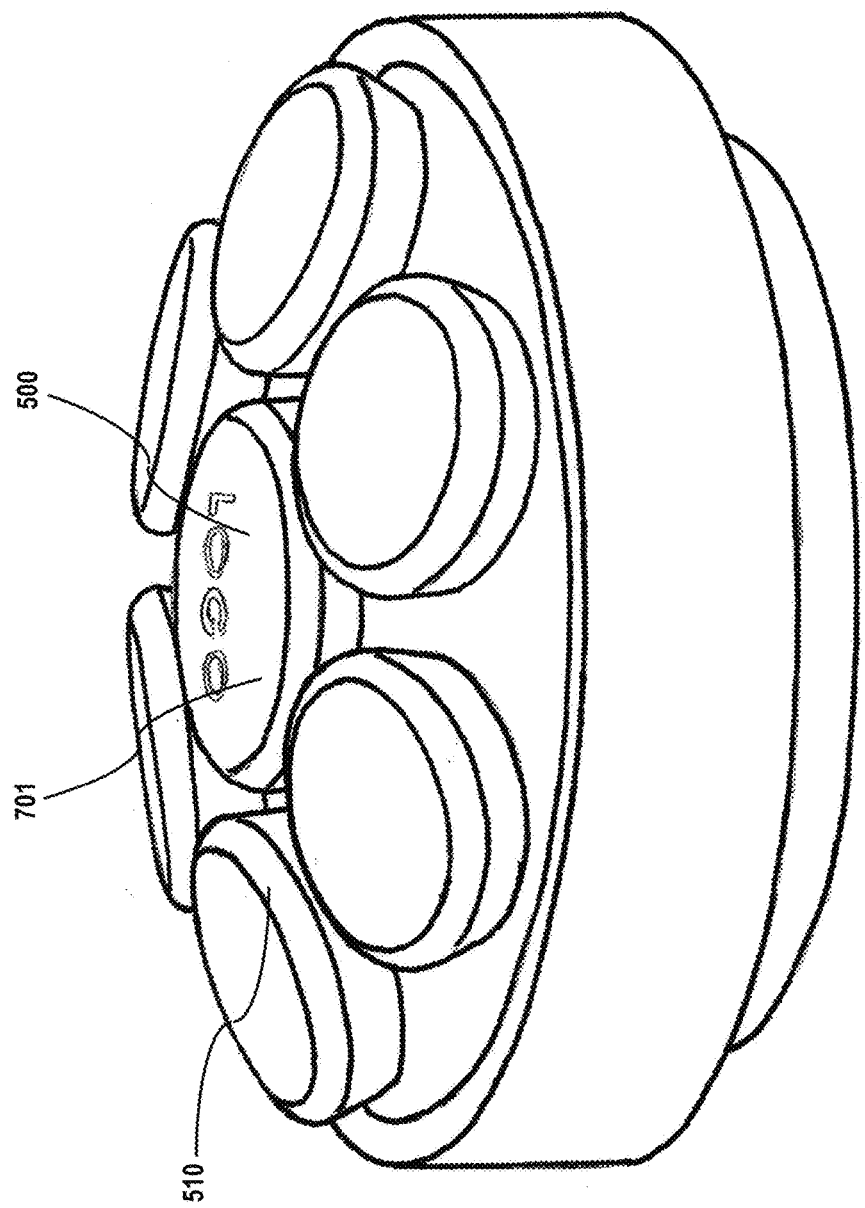
FIG. 8 is a top perspective view of a portion of another example apparatus for dispensing a controlled amount of an additive into the contents of a container in accordance with one or more embodiments described herein.

FIGS. 7 and 8 show additional details of the alignment and "seating" of the vessels containing additives in accordance with one or more embodiments of the present disclosure. FIG. 7 illustrates a centralized dispensing mechanism, in communication with onboard software and/or a secondary device for the purpose of orienting the dispensing mechanism upon the desired vessel, and further, to trigger action from the dispensing system to modulate the force applied to the vessel and the frequency with which the force is applied, to precisely deploy the desired quantity of additive and achieve the correct concentration.

It should be understood that, in accordance with one or more embodiments of the present disclosure, the additive vessels may be arranged or positioned in a manner other than radially. For example, the additive vessels may have a linear orientation, hexagonal orientation, or some orientation other than radial. In addition, with such alternative arrangements of the additive vessels, the dispensing mechanism may include more than one (e.g., multiple) pressure actuators or pistons which act upon one vessel or may act upon multiple vessels simultaneously to dispense the additives contained therein.

The dispensing system may modulate the displacement-volume, displacement-force, and/or displacement-frequency accordingly to control the quantity or volume of additive dispensed. Displacement-volume refers to a temporary change in the volume of an additive vessel (either positive or negative) as a result of the action of a dispensing system in order to release a corresponding volume of additive. Displacement-force refers in this case to variability in the dispensing mechanism's output strength as a moderator of dispensing volume, force might be varied for instance to ensure precise dispensing of a more viscous additive, as the instantaneous pressure applied to the container would be a significant factor. Displacement-frequency refers to the overall number of cycles over a period of time that the dispensing mechanism acts upon the additive vessel, a higher frequency correlating directly to a higher number of droplets ejected as a consequence.

An additional factor which may play a significant role in the accuracy of additive dispensing is that of piston recoil. The pressure actuator piston strikes the additive container to dispense the additive, however, where a droplet forms more slowly, the recoil may be calibrated to occur more rapidly, thus inducing a pulsatile pressure application that forces the creation of a droplet (and mitigating the likelihood of a larger less-precise droplet forming from any surface-tension interaction etc.). In other situations or scenarios, the opposite may apply such that pressure is needed to "dwell" on the vessel to produce a successful dispensing event.

FIG. 8 shows a further embodiment of a dispensing module and additive vessels in which the additive vessels are almost fully enclosed by retaining walls and are also oriented close to a vertical position in order that gravity may assist in additive dispensing.

While the system and apparatus described in accordance with one or more embodiments of the present disclosure may be implemented in the form of a portable water container, it should be understood that the scope of the present disclosure is not limited to the specific context of a water container. In accordance with one or more other embodiments, the systems and apparatus may be implemented (e.g., mounted, installed, or otherwise put in communication with) in conjunction with other systems for dispensing additives selectively and accurately. In addition, although the various examples provided herein describe a system generally mounted within the uppermost section of a water bottle, the dispensing system may be mounted in a multitude of configurations, including but not limited to: in the side, on the bottom of the device, or on the top of the device.

Similarly, the embodiment of the dispensing module and consumable container may be in a non-portable form factor, such as an arrangement optimized for location on a kitchen counter-top or a retail kiosk.

Figure 9:
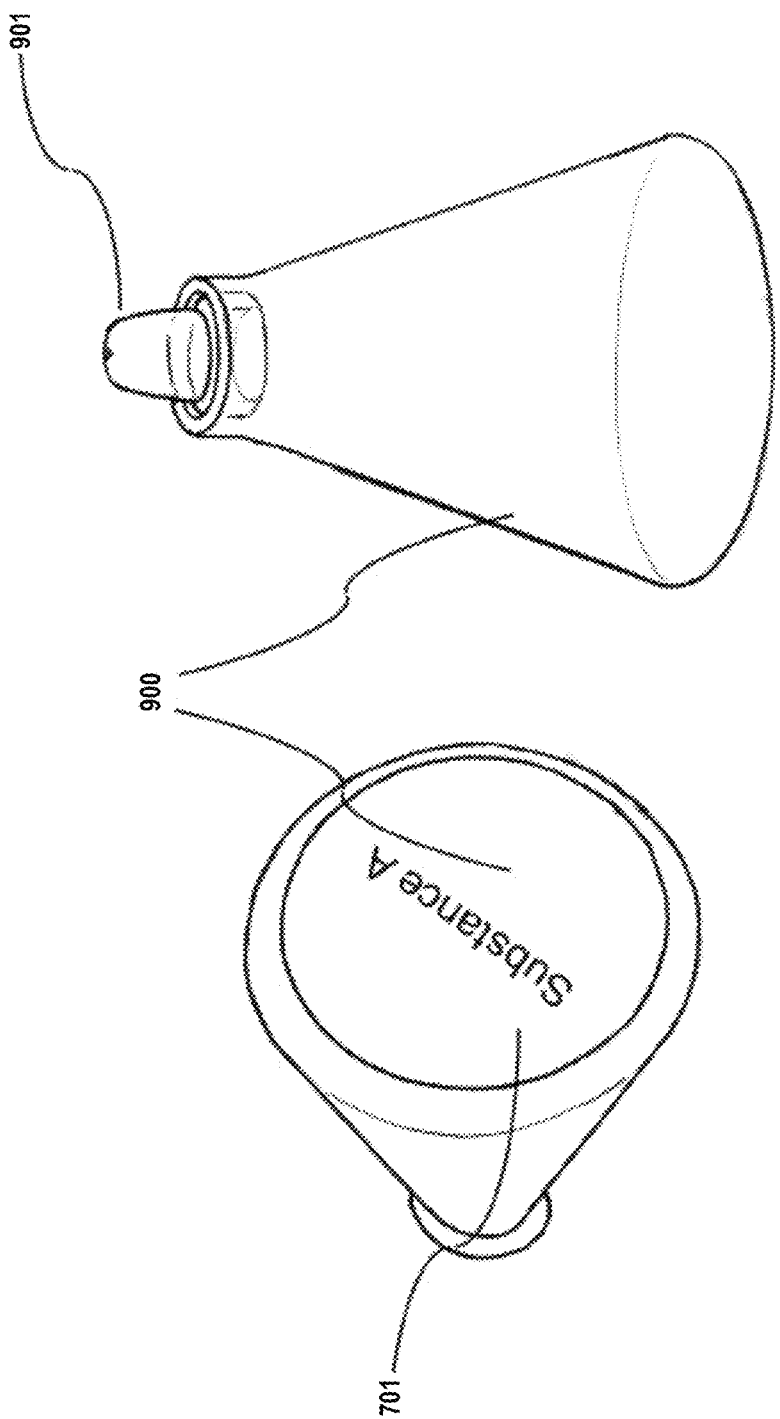
FIG. 9 illustrates an example of an additive vessel in accordance with one or more embodiments described herein.

FIG. 9 illustrates an example of an additive vessel 900 in accordance with one or more embodiments described herein. For example, the additive vessel 900 may include a dispensing nozzle 901 with a pore designed to optimize drop size/volume, the nozzle 901 being connected to the additive vessel 900 via a tapered cylinder in order to optimize drainage and flow-rate.

Figure 10:
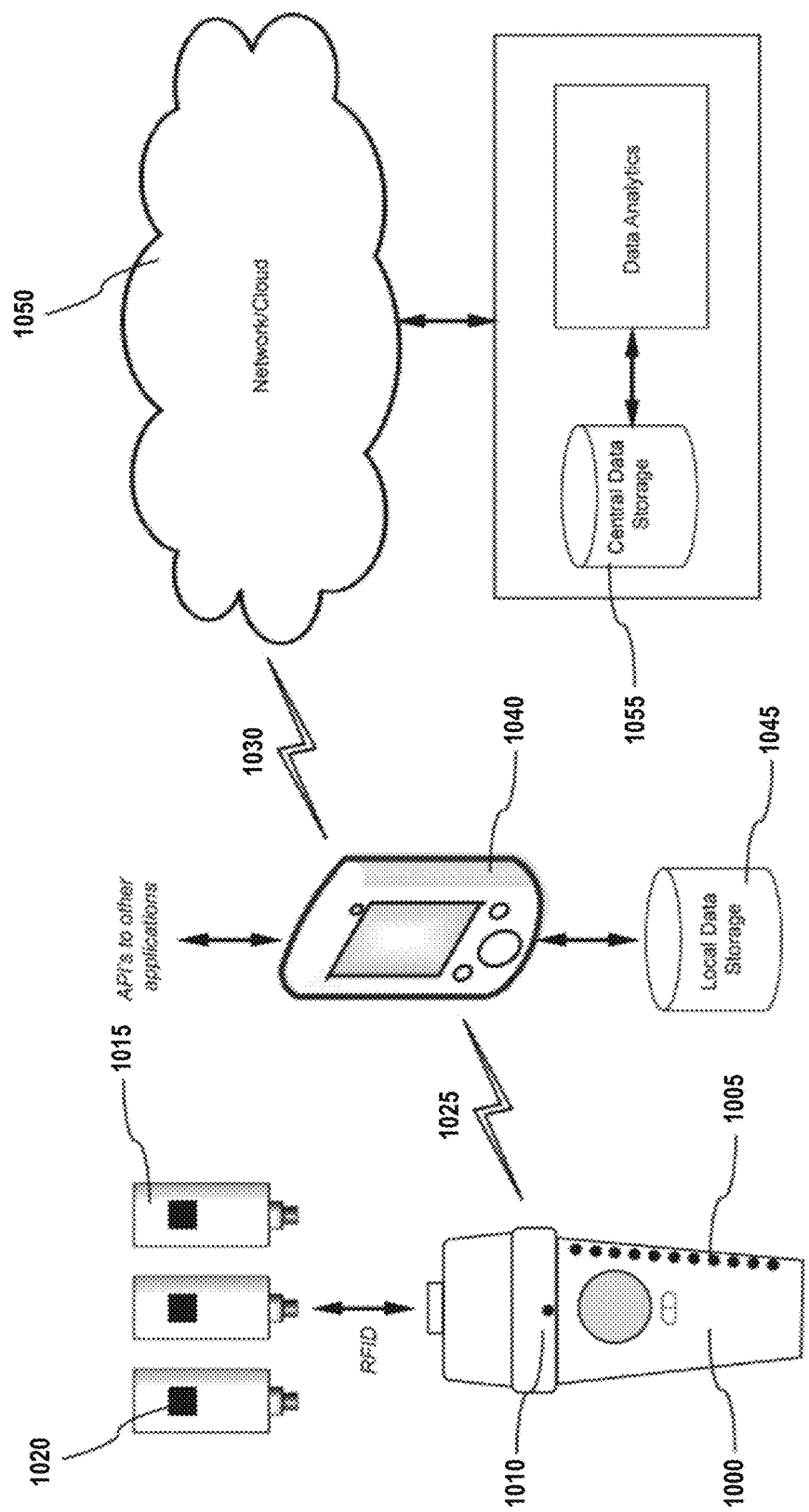
FIG. 10 is a block diagram illustrating an example system and surrounding environment in accordance with one or more embodiments described herein.

FIG. 10 illustrates an example of an overall ecosystem within which one or more embodiments of the present disclosure may have application and/or may be implemented. FIG. 10 includes a container 1000, generally but not necessarily portable, that may contain a consumable (e.g., a liquid) into which liquid, powder, and/or other forms of additives may be dispensed from one or more separate removable additive vessels 1015. Data about the additives within each vessel 1015 may be encoded within a RFID or similar type tag 1020 mounted on or otherwise attached to the additive vessel 1015. Such data about the additives contained within the vessels 1015 may be read from the RFID tag 1020 by, for example, an RFID or similar-type antenna that is a component of a dispensing module within the container 1000. For example, in accordance with at least one embodiment, the container 1000 may include an RFID antenna (not shown) that rotates around a central axis of the container 1000 to individually or sequentially read data from the RFID tags 1020 on the additive vessels 1015. In this manner, data about the additives contained in the additive vessels 1015 may be collected, analyzed, and/or communicated by the container 1000 (e.g., by a processor and/or other components of the container 1000), and made available to one or more user devices 1040, storage systems or networks 1045, 1055, and the like by means of local wireless communication 1025 and/or wide area wireless communication networks 1030.

Furthermore, in accordance with one or more embodiments, a linear capacitive sensing strip, or other liquid level reader 1005 may be mounted within or adjacent to the chamber of the container 1000 within which a consumable liquid may be stored (e.g., retained, contained, etc.). The linear capacitive sensing strip, or other liquid level reader 1005 may be configured to determine the level, volume, or quantity (e.g., the amount) of liquid consumable in the container 1000 at any given time. As such, data about the consumable liquid in the chamber of the container 1000 may be collected, analyzed, and/or communicated by the container 1000 (e.g., by a processor and/or other components of the container 1000), and made available to one or more user devices 1040, storage systems or networks 1045, 1055, and the like by means of local wireless communication 1025 and/or wide area wireless communication networks 1030.

In addition, data about a user of the container 1000 may be accessible to and/or obtainable by the container (e.g., by a processor or other component of the container 1000). For example, the container 1000 may receive (e.g., retrieve, access, request, or otherwise obtain) data about the user that is stored, for example, in one or more databases or storage devices 1045 local to the user, within an application residing on a device of the user 1040 (e.g., a portable user device, such as a cellular telephone, smartphone, personal data assistant, laptop or tablet computer, etc.), and/or in network/ cloud data storage 1050, 1055. In accordance with at least one embodiment of the present disclosure, the data about the user may include, for example, user demographic information (e.g., age, gender, weight, body mass index, etc.), additive purchase history information, additive usage history information, charge/payment information for purchases, and various other data associated with the user or actions of the user. In this manner, such data about the user of the container 1000 may be collected, analyzed, and/or communicated by the container 1000 (e.g., by a processor and/or other components of the container 1000), and made available to the device of the user 1040, to one or more other devices of the user, to the one or more databases or storage devices 1045 local to the user, to the network/cloud servers and data storage 1050, 1055, and the like.

In accordance with at least one embodiment described herein, one or more APIs (Application Programming Interfaces) from a mobile device application associated with the container 1000 may interface with and access data from other applications running on a device of the user (e.g., user device 1040), where such data may include, but is not limited to, geo-location, time, local weather conditions, temperature, personal schedule (e.g., from a calendar application), etc. APIs to third party applications may also be used by the container 1000 to access user data about the recent physical activity of the user. For example, data may be obtained from a variety of existing or future personal physical activity tracking/monitoring devices (e.g., Fitbit, Apple Healthkit, etc.), any of which can furnish various data related to physical activity of the user. Some non-limiting examples of the type of data that may be obtained from such physical activity tracking/monitoring devices include data about the type of physical activity undertaken by the user, the number of steps taken by the user during a period of time, speed of motion, estimated energy expenditure (e.g., calories burned), etc. Accordingly, data about the user's physical activity levels and activity history may be collected, analyzed, and/or communicated by the container 1000 (e.g., by a processor and/or other components of the container 1000).

All or a portion of the data described above may be communicated to or otherwise retrieved by one or more processors which may be located within the consumable container 1000 or external to the consumable container 1000 (e.g., in the user's mobile device 1040, in the cloud network 1050, etc.), where the data may be used to derive more specific and focused patterns and trends about an individual's activity, purchase, and/or consumption behaviors.

In accordance with one or more embodiments of the invention, the apparatus of the hydration system of the present disclosure may be in communication (e.g., via a wired or wireless network) with a separate device (e.g., a user's mobile device, such as user device 1040 in the example ecosystem shown in FIG. 10) acting as an ancillary user interface and/or providing processing capability, and/or communicating data to and from external sources to further inform and/or optimize the dispensing of an additive. This may leverage API data, hardware sensor data and other data to develop contextually relevant dispensing schedules. For example, the system may communicate with one or more other devices to update and/or inform firmware/software or a processor within the hydration device to increase a concentration of "Substance A" by a certain percentage or amount (e.g., 10%) while decreasing a concentration of "Substance B" by the same or different percentage or amount (e.g., 16%). As another example, further updates received by the system via communications with one or more external devices might include a temporary increase in the amount of "Substance C" dispensed due to, for example, by increased physical activity. Such a temporary increase may apply to a single dispensing event or to multiple subsequent dispensing events.

In accordance with at least one embodiment, the hydration system of the present disclosure may log (e.g., store in a memory) a user's consumption habits over time. This may be used to inform the user of behavioral and/or consumption adjustments and/or future purchasing recommendations. For example, the system may maintain a history and/or log of purchase history as well as consumption rates of vessels containing additives and this data may be further correlated with user physical performance, subjective user feedback, and other key metrics relating to a user's physical performance, physical well-being, mental well-being, and other objective or subjective factors pertaining to the user's quality of life. This consumption history and/or log may be used to further inform and/or optimize future dispensing of additives, future purchase recommendations, etc. In a further example, the system may obtain information about changes in a user's physical performance by means of APIs to other software applications on the user's mobile device or other associated platform (e.g., data pertaining to the user's endurance, strength, recovery, etc.) this may be used to determine the effectiveness of fitness-related additives that the user has consumed. As another example, a weaker caffeine additive or a lower concentration of an existing caffeine additive may be recommended and/or dispensed after the system detects information which indicates that the user is experiencing decreased sleep quantity/quality.

In accordance with at least one embodiment, objective performance as assessed by direct and indirect measurements may be further correlated against more subjective feedback provided by the user. For example, such subjective feedback may be provided by the user via a user interface which is a part of the hydration device and/or which is part of an associated mobile device. This subjective input data received from the user may be subsequently quantified and correlated against passively obtained implicit data (e.g., via software API) and actively obtained explicit data (e.g., via an associated hardware sensor device or direct user input).

User-specific performance and/or preference data may be stored internally to the hydration device (e.g., using an internal memory of the device) and/or externally to the hydration device (e.g., in a cloud repository such as part of an eCommerce website, remote computer, associated mobile device, etc.). Such user-specific data may include, for example, data about the user's consumption rates of various additives, day and/or time patterns of consumption by the user, physical activity levels of the user (which may for example, be obtained from one or more measuring instruments or devices either integrated into the hydration apparatus or separately connected to the apparatus including, for example, an accelerometer, power meter, pedometer, etc.), geographic locations associated with the user's consumption of additives, heart-rate variability, other associated health data, demographic information of the user, and the like. For example, the system may leverage both GPS and API data to inform and optimize the dispensing of additives to a user; if the user is at the gym, the dispensing system may dispense additives containing more electrolytes, and/or may prompt the user to consume more water.

The portable hydration device system may also dispense additives according to schedules, other real-world information pertaining to the temporal-dynamic of a user's lifestyle, and other dynamics pertaining to a user's overall mental and/or physical state. For example, the system may optimize the daily schedule of dispensing of additives based on a time that a user wakes-up. In such an example, in addition to leveraging data from a secondary device of the user (e.g., an alarm clock application) regarding the user's wake-up time, the dispensing system may supplement the data based upon the activation of an onboard sensor (e.g., an inertial sensor) to inform the system of a direct user interaction with the hydration device (thereby increasing the accuracy of the data).

In accordance with one or more embodiments of the present disclosure, such secondary device data may be obtained from a wearable device (e.g., a wearable technology device that may be directly or indirectly in communication with the hydration device) and may additionally be combined with data from other third-party APIs, health data, ambient conditions, manually entered user parameters and/ or fitness/wellness goals, etc., to optimize the delivery of nutrients, supplements, vitamins, and hydration in response to a user's activities and physical status.

With existing wearable devices and systems, a user is required to analyze and interpret the basic output data in order to determine the actions or behavioral changes which might be appropriate in order to adjust additive intake to positively impact physical performance parameters. Consequently, any alterations or adjustments made to the user's hydration or nutrition/supplement/vitamin consumption will likely be guesses and approximations.

In contrast to such existing approaches, the systems, methods, and apparatuses of the present disclosure automate the collection, analysis, interpretation, and adjustment processes with respect to the various data and the environmental and other factors that may be collected and measured by wearable technology devices. Such data and factors may include, for example, measurements of energy output, physical activity, heart-rate, number of steps taken etc., ambient conditions which may impact a user's physical well-being, such as ambient temperature and humidity, geographic data pertinent to a user's hydration and/or nutritional requirements, daily, cumulative, peak and/or current physical activity levels, GSR (skin conductivity), and the like.

For example, where data from one or more devices provides indication of a strenuous muscle building exercise, the dispensing system may respond by selecting a type and quantity of additive optimized for recovery and muscle building. The system might also work to keep other physiological parameters of the user within optimized ranges via inferential optimization, making recommendations and automated adjustments to keep the user within a certain peak and/or optimized physical state, for example, the amount of caffeine dispensed may be decreased if data from an associated wearable device indicates that user's heart-rate is unusually high. In another example, on a hot day the system may make an adjustment to the type and/or quantity of additive dispensed based on the user's physical activity levels and the ambient temperature, humidity, UV levels, and/or other weather or environmental factors to increase the electrolyte dispensing rate.

In accordance with at least one embodiment, the hydration device may be in communication with an associated wearable technology device. Such devices are capable of monitoring and measuring human physical activity and certain biometric parameters. Biofeedback data generated from such monitoring and measuring functions may include, for example, heart rate, GSR (Galvanic Skin Response), skin temperature, blood flow, etc. Therefore, in accordance with one or more embodiments described herein, a biofeedback loop may be created whereby the biometric measures detected by a wearable device in response to the intake of vitamins, medicines, and/or dietary supplements etc. using the dispensing and delivery system of the present disclosure may be wirelessly communicated to an application residing on a mobile device, from which it may be further communicated to a remote or cloud-based data repository.

An API between this application or cloud-based repository enables the instantaneous and longer-term biofeedback response patterns to be analyzed and used as an input to the specification, recommendation, or fine-tuning of subsequent product purchases (e.g., the online purchasing of vitamins and dietary supplements and the like). This biofeedback based fine-tuning is a fundamental part of the strategy of achieving a user-specified wellness or nutritional goal.

In a similar manner, the system of the present disclosure may additionally or alternatively leverage data obtained via an API to a dedicated medical application and/or from medical device hardware to adjust or modify the dispensing of additives in the short term and also to inform purchase recommendations in the longer term.

For example, a user with diabetes may have and use a glucose-meter. Data from the glucose-meter may be communicated to the hydration device and the dispensing of additives adjusted to help maintain appropriate blood glucose levels. Data may also be communicated to a physician portal or application and further communicated to an e-Commerce system in order to ensure that future purchases are appropriate for or optimized for the specific needs of that diabetic user.

Furthermore, the hydration, delivery, and dispensing system may correlate data relating to physical activity, hydration and other user and environmental factors with data from the glucose-meter or other medical hardware device to responsively dispense an optimal concentration of additive to avoid adverse responses to non-optimal glucose levels.

In another example, a user may be on a blood thinning regimen and may need to consume an aspirin-infused additive throughout the day, this may be prescribed, recommended and/or ordered in a similar manner to the aforementioned and dispensed throughout the day. The amount dispensed may be adjusted based on blood pressure measures obtained from an associated (connected) blood pressure monitoring device and may therefore vary between different dispensing events.

A signal or prompt from a processor (e.g., either integrated within the hydration device, or communicated wirelessly from an associated mobile device) instructs the dispensing module to act upon one specific chamber or vessel and dispense a specified quantity of droplets, or in the case of a solid, to maintain an opening for a powder or other solid form factor to drain into the solute at a variable rate. The internal firmware of the hydration device, coupled with the software on an associated mobile device, in conjunction with data from the device's sensors calibrates dispensing accordingly. The following are some example, non-limiting, parameters that may define the quantity of additive dispensed in order to achieve a specific level of concentration:

(i) The hydration container is filled to 50% volume, the quantity of droplets (or other dispensing modality, e.g., stream, drop, spray, etc.) is adjusted to maintain an appropriate or user personalized concentration (e.g., in this example decreased by 50% since the container is only half-full).

(ii) Subjective feedback from the user, including direct input by the user and/or data indirectly accessed from biometric sensors, wearable devices, or other similar means, etc., informs the system that the previous "mix" was weaker than the user preferred, consequently the quantity of droplets (or other dispensing modality, e.g., stream, drop, spray, etc.) is increased for the next dispensing event.

(iii) Subjective user feedback, input via a user interface on the hydration device or other connected device, directly requests an increase or decrease in overall strength or concentration of additive prior to a dispensing event, the amount of additive dispensed is modified for future dispensing events.

(iv) Data from a wearable device, or API to a third party application on a user's mobile device indicates that the physical exertion of the user of the hydration device has greatly increased, indicating a need for more of "Substance X" (e.g., a fitness/recovery additive). The processor communicates to the dispensing module to dispense an increased quantity of "Substance X" at the next scheduled dispensing event.

(v) Data from APIs, direct measurement, and/or user input informs the processor and thence the dispensing mechanism of a need to increase or decrease the consumption of a specific additive (for example, intake of zinc, iron, glucose, or protein). The dispensing mechanism and its coupled firmware subsequently adjusts the dispensing quantity accordingly.

The hydration and dispensing system described herein may operate in conjunction with an associated secondary device, but may additionally or alternatively operate independently and without requirement of a secondary device to deliver prompts or dispensing data.

To further illustrate some of the features of the various embodiments presented herein, the following describes a number of example use cases of the hydration systems, methods, and apparatuses of the present disclosure. It should be understood that although the following examples are presented in particular contexts and include certain specific design parameters of the systems and apparatuses, the scope of the present disclosure is not in any way limited to the particular contexts, implementations, or specific design parameters described.

In a first example, suppose a user loads vessels containing different additives into a hydration device, such as a water container, and suppose that user wakes-up at 7:00 AM. The user may be prompted by the hydration device (or associated mobile device) to fill the container with "X" ounces (oz.) of water in order to hydrate properly. The dispensing system of the device may then dispense a caffeine and B-vitamin complex to promote wakefulness and energy during the morning. Later in the day, the system may obtain information from the users calendar or other applications which indicate that the user is in a long meeting. Accordingly, the system may calibrate hydration levels and glucose levels to ensure that the user will not prematurely require a bathroom break during the meeting (e.g., where the system has knowledge of the user's typical urination frequency or data about the user's most recent use of the bathroom), and also to help ensure that the user remains alert and attentive throughout the meeting.

In a second example, a user may go to the gym after work and the system may be informed about this based on GPS coordinates and/or other data obtained from API's to calendars, personal schedules, and/or other data sources pertaining to a user's activities, routines, etc. which may be accessible on the user's mobile device or in the cloud. Accordingly, the system may prompt the user to hydrate more and may dispense a "pre-workout mix" containing additional electrolytes as soon as the geo-location data indicates that the user is at the gym.

In a third example, each member of a sports team may have and use a hydration container which may be in wireless communication, via the user's mobile device, with a centralized application residing on the mobile device or computer of the team coach. The coach may set hydration targets, additive consumption targets and such like for each team member in order to optimize performance. The coach may also monitor and adjust consumption targets and behaviors in near real-time, sending updated data and targets wirelessly to the individual hydration containers.

Physical activity data, time and/or a change in geolocation may indicate that the user has reached the end of his workout session, in response the hydration device may dispense one or more additives optimized for a post-workout. Later that evening, the hydration device may access data relating to the user's next day schedule and/or desired wake-up time and may dispense a sleep aid at the optimal time to help ensure a good night's rest.

Figure 11:
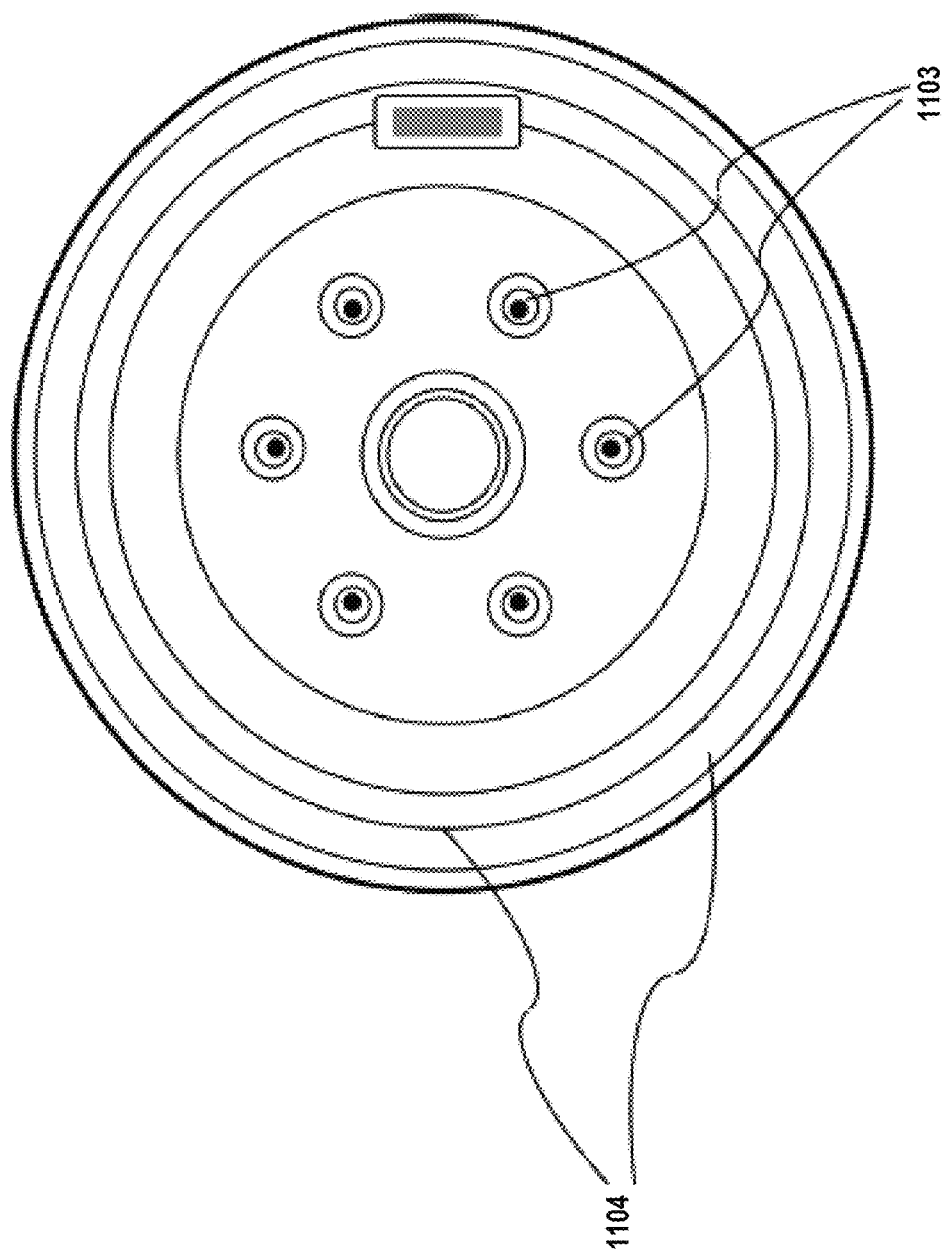
FIG. 11 is a bottom view of an example apparatus for dispensing additives into the contents of a container, showing dispensing nozzles of additive vessels mounted within a lid assembly of the apparatus in accordance with one or more embodiments described herein.

FIG. 11 illustrates a bottom-view of the example additive vessels shown in FIG. 10 and described above. Shown are the nozzles 1003 of the additive vessels extending through the base of the dispensing module, thus keeping the nozzles and the dispensing assembly from coming into direct contact with the fluid in the container. This also ensures more optimal placement of the nozzles 1003 in order that additives drip into the central area of the container rather than running down the sidewalls. In addition, in accordance with at least one embodiment, the dispensing module may include tabs 1004 that act as mechanical position markers to define the axial rotation of the additive vessels or pressure actuator (depending on which is moving and which remains stationary), and enable the automatic detection and identification of the additive vessels 1001.

Figure 12A:
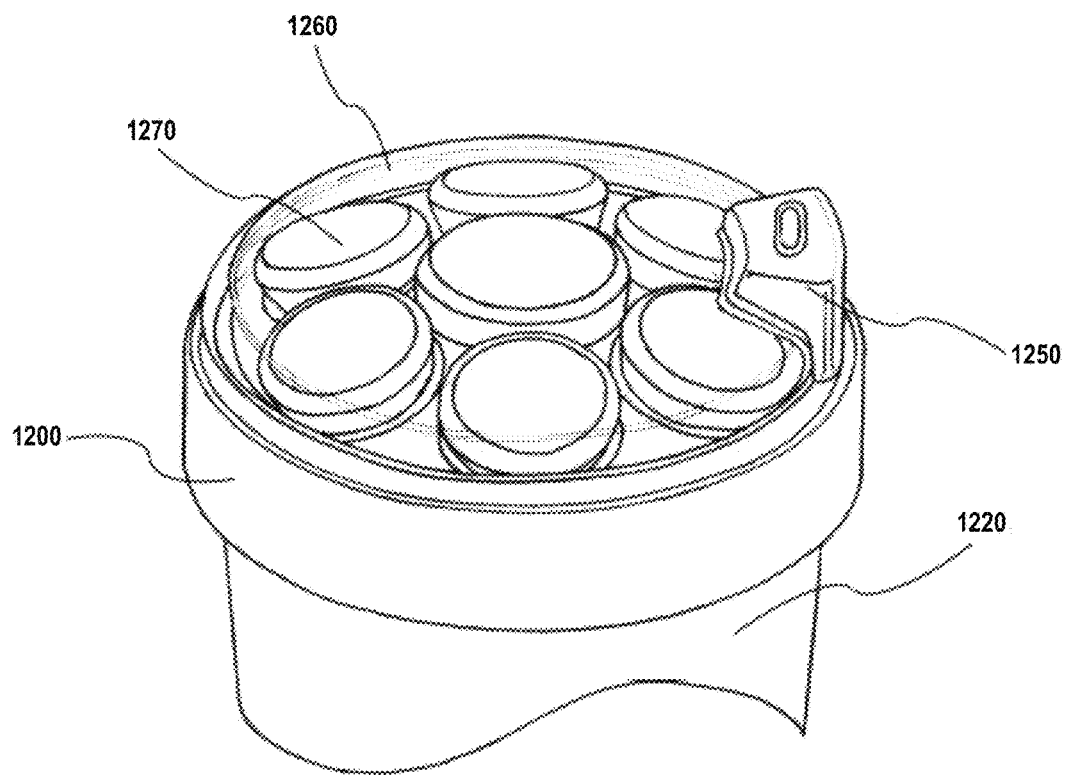
FIG. 12A is a top perspective view of an example dispensing module mounted above a portion of a hydration container in accordance with one or more embodiments described herein.
Figure 12B:
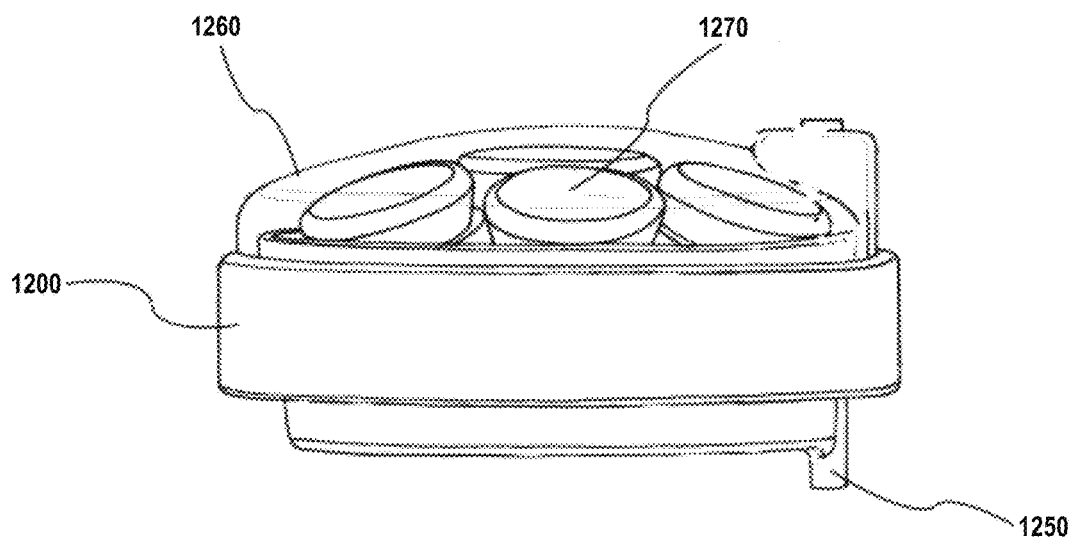
FIG. 12B is a side perspective view of the example dispensing module shown in FIG. 12A, with the portion of the hydration container removed in accordance with one or more embodiments described herein.

FIGS. 12A and 12B show an example of the dispensing system of the present disclosure in an additional context. For example, in accordance with one or more embodiments described herein, the dispensing module or system 1200 may be oriented above a cup, bottle or container 1220 carrying a solute. In at least the present example, the dispensing module 1200 includes an opening for the passage of a straw or drinking channel 1250 (which may or may not be a part of, or an accessory to, the dispensing module 1200). The straw or drinking channel 1250 may comprise or be accompanied by an in-line flow-meter (not shown). In addition, the dispensing system 1200 may include or may be used in conjunction with a protective cover 1260 (represented by a transparent wire frame) that isolates and protects the system and covers the additive vessels 1270. FIG. 12B shows further details on the placement/housing of the dispensing system 1200, including the exit passage of the straw 1250 placing the system 1200 within the cup/bottle/vessel 1220 containing solute, while isolating the flow-meter within the technology module, sealed for durability.

Figure 13A:
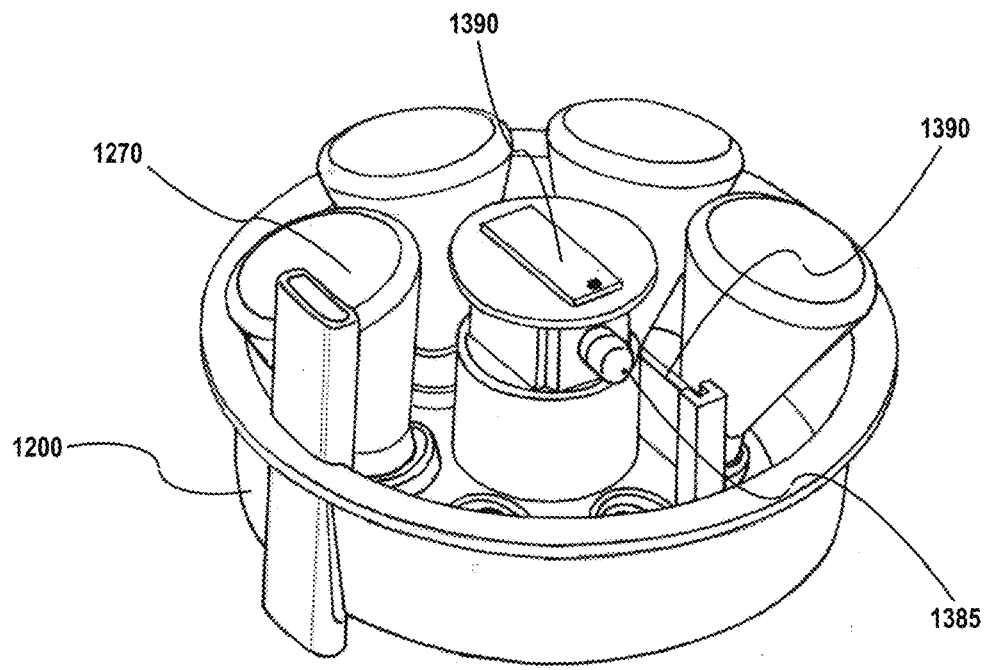
FIG. 13A is a top perspective view of an example additive dispensing module with several additive vessels mounted therein in accordance with one or more embodiments described herein.

FIG. 13A is a cutaway view of the example embodiment of the dispensing system shown in FIG. 12, with components of the system removed and/or stripped-down to illustrate typical locations of various internal components of the system. For example, the dispensing system 1200 may include one or more chips or processors 1390 configured to perform various operations of the dispensing system described herein. FIG. 13A also illustrates the input component 1385 of the actuator piston (e.g., actuator piston 504 in the example system 500 shown in FIG. 7) with a shape optimized to provide progressive displacement of the additive vessel 1270.

Figure 13B:
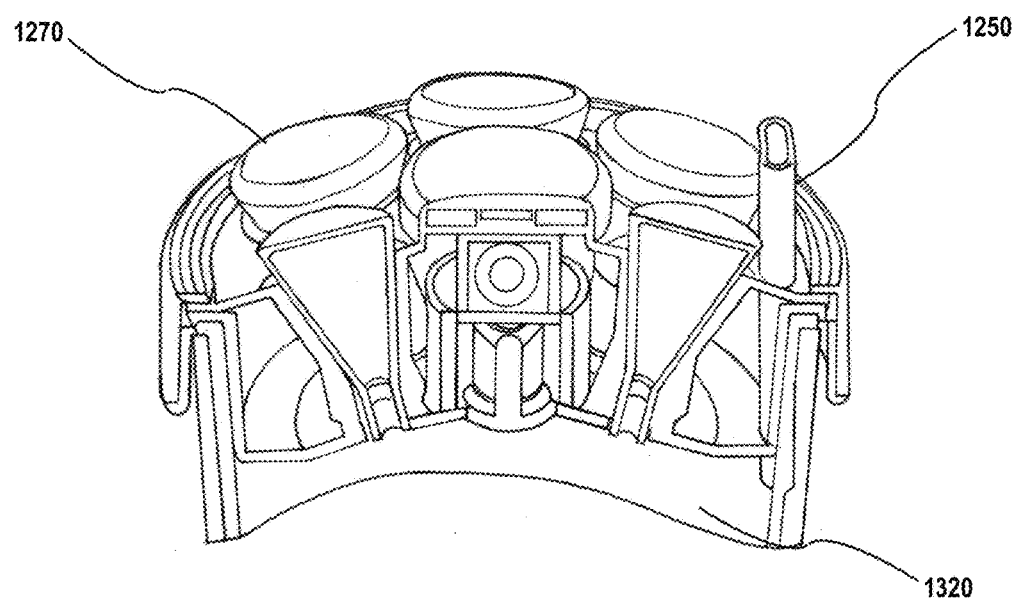
FIG. 13B is a cross-sectional side elevation view of the example additive dispensing module shown in FIG. 13A in accordance with one or more embodiments described herein.

FIG. 13B is a cross-sectional view of the example dispensing system and illustrates the locations of various components of the dispensing system 1200 with respect to one another. As described above, the centralized piston assembly (e.g., actuator piston 504 in the example system 500 shown in FIG. 7) acts upon the additive vessels 1270 to selectively apply pressure and precisely dispense the contents into the cup, bottle, container or vessel 1320 above or below (or in another orientation in direct or indirect communication with the dispensing assembly).

Figure 14:
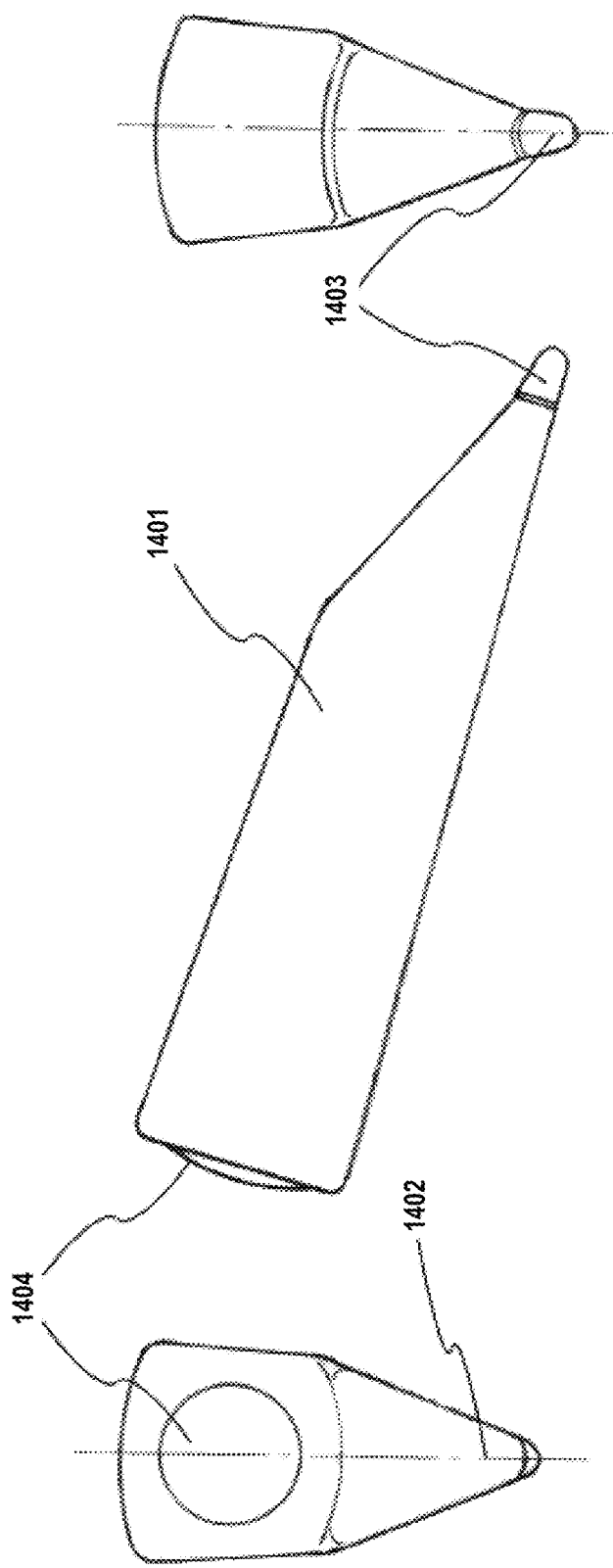
FIG. 14 illustrates another example of an additive vessel in accordance with one or more embodiments described herein.

FIG. 14 illustrates a further example of an additive vessel 1401 comprising a generally tapered form and a substantially triangular cross-section, with an apex at the lowermost position 1402. This form factor maximizes the flow of the additive contents of the vessel towards the dispensing nozzle 1403. The additive vessel may also have a more compressible or compliant concave or convex subsection 1404 of one of the outer walls positioned such that pressure actuator applies pressure in the center of this more compressible or compliant area. This may additionally be of a high friction material in order to ensure maximum efficiency in pressure transfer as well as minimizing the risk of the pressure actuator slipping against the vessel wall. A plurality of these additive vessels may be mounted axially around the center line of the hydration device, with the dispensing nozzles innermost and sloping towards the center line in order to maximize drainage of additive into the contents of the container and the beneficial effects of gravity.

In accordance with one or more embodiments, the system may comprise an E-Commerce system from whence a user may purchase additives, additive vessels and other products related to the hydration device. In addition, the E-Commerce system may recommend products to the user based on the aggregation of data from multiple sources and/or multiple users providing insights into general physical activity levels and patterns (eg from wearable activity devices), environmental conditions, ambient conditions (eg from applications residing on an associated mobile device), and the like. This data may be combined with direct user inputs pertaining to the aforementioned parameters/factors, as well as additional data which may include, for example, more subjective input data which may be subsequently quantified. The user data aggregated from multiple users may then be correlated with an individual user's requirements/goals/lifestyle to generate purchase or behavioral recommendations with the aim of optimizing key metrics for the user such as, for example, sleep, physical performance, mental well-being, and other indices more broadly related to the quality of a user's life.

Furthermore, products may be recommended to a user based on activity and/or consumption data provided by the system using various algorithms known to those skilled in the art. These may include, for example, collaborative filtering algorithms whereby products are recommended based on the purchase, use, or consumption patterns of other users with comparable age, demographic, or activity parameters. For example, suppose a user has purchased additives A and B. If people who have used additives A and B also have used additives C and D, the latter may be recommended to the user as potential purchases even though the user has not previously purchased additives C and D. In a further embodiment, product recommendations may be based on their similarity with previously purchased or consumed additives. For example, additives X and Y may be recommended because they have properties which are similar to additive Z, which has been previously purchased and consumed by the user.

In a further embodiment, since the amount of additive content in an additive vessel is known and the rate of dispensing of that additive is also known, then the system may estimate or predict when an additive vessel will become empty. This information may be used to automatically place an order to purchase more of that additive or to place that additive in a user's shopping cart on an E-Commerce website and/or to inform the user, via a display on the hydration container and/or on the user's associated mobile device, that supplies of that additive will soon be depleted. The user may additionally have the option of initiating or confirming that online purchase directly from the hydration container using the user interface elements provided thereon.

In accordance with at least one embodiment of the present disclosure, the recommendation engine may additionally include a system that prompts behavioral adjustments for an user based on information derived from detection of the locations that a user visits. For example, a user might visit a restroom, and the geo-location data used to identify that the location is in fact a restroom, this in turn may trigger a timer which measures the length of time that the user is in that location. With the additional use of physiological data (e.g., key parameters such as height, weight, age, gender, allergies, illnesses, exercise frequency, and other factors relating to the physical state of an individual) manually entered by the user, the system may estimate urine output and thence the user's hydration levels.

Such hydration level data may form an additional input to a recommendation algorithm. Such physiological data may be manually entered and/or may be collected via sensors associated with a device of the user, from a third-party API, or through various other channels. Furthermore, the same data may be collected from more than one source in a redundant manner to increase accuracy.

This system may also make determinations related to regularity of visits to the restroom to infer stress levels, and/or to formulate predictions that might be protective/preventative regarding the user's health.

In a further example, the location data may determine that the user has entered a specific restaurant and may access online menu information to recommend the most appropriate meal based on user defined health and fitness goals and prior nutritional intake, thereby optimizing food and nutritional intake for the user. If menu data is unavailable, the system may instead recommend specific food types and quantities, leaving the user to choose the specific menu item comprising those food types. in a further example, location data may determine that the user has entered a gym or similar fitness location and may adjust the dispensing of specific additives or supplements up or down and adjust hydration recommendations accordingly.

In accordance with at least one embodiment, the hydration and dispensing systems, methods, and apparatuses of the present disclosure may additionally comprise a light quality/quantity sensor that assesses exposure to Ultra-Violet (UV) and/or other radiant energy that might affect the mental and/or physical well-being of the user. Data on UV levels obtained from the sensor may be used as an input to an algorithm which may determine optimum nutrition and/or hydration requirements. For example, Vitamin-D levels are effected very directly by exposure to sunlight, therefore the quantity and timing of the dispensing of Vitamin-D supplements to the user may be adjusted upwards or downwards in response to the level of exposure to UV measured by an integrated sensor device and/or derived via an API to a third party application on an associated mobile device or accessed from the cloud. The system may also provide recommendations for behavioral adjustments based on the levels of UV exposure such as the ideal timing for the application of sunscreen, etc.

In a further embodiment, the system may leverage GPS in the hydration device and/or an associated user device to determine the user's geographical location and thence the environmental conditions of that user by means of APIs to existing online data sources (e.g., weather forecasting websites). Thus the user's environment may be quantified in terms of ambient temperature, humidity, UV exposure, environmental pollutants, dust and allergen levels, etc., and taken into account when determining nutrition and/or hydration levels.

For example an API to an activity or location application might indicate that the user is moving at a speed consistent with jogging, while a weather application indicates that the ambient temperature at that location is ninety degrees fahrenheit, with a relative humidity of 80%. This would indicate that the amount of liquid that the user should consume will need to increase above that which might previously have been scheduled or recommended and that adjustments may need to be made to the additive dispensing schedule in terms of which additives are dispensed, the timing and the quantities.

The hydration and dispensing system of the present disclosure may additionally inform a user about sleep cycle decisions by guiding the user towards optimized exposure to sunlight or artificial light-sources for the purpose of improving/optimizing sleep quality or quantity. In addition, the system may also leverage camera data from a user's device (e.g., mobile telephone, smartphone, tablet computer, etc.) to make determinations and subsequent recommendations based on skin darkness/lightness and inferred melanin density, for the purpose of a more accurate, user-specific recommendation. In accordance with at least one embodiment, the system may also use geographical location and local time data to determine whether a user has substantially changed location within a short timeframe and may be affected by jet-lag. This data may be used to further adjust or modify the nature, timing and/or quantity of dispensed additive to compensate accordingly and to help restore diurnal rhythms.

In accordance with at least one embodiment of the present disclosure, the hydration and dispensing system described herein may be implemented as part of a water bottle or other portable hydration device. This may comprise, among other components, a user interface screen or display that is a part of the container itself or an accessory component thereof. A processor within the container may be in communication with a separate connected mobile or wearable device and with the interface screen or display for the purposes of displaying to the user, relevant instructions, guidance, information, data and the like.

Figure 15:
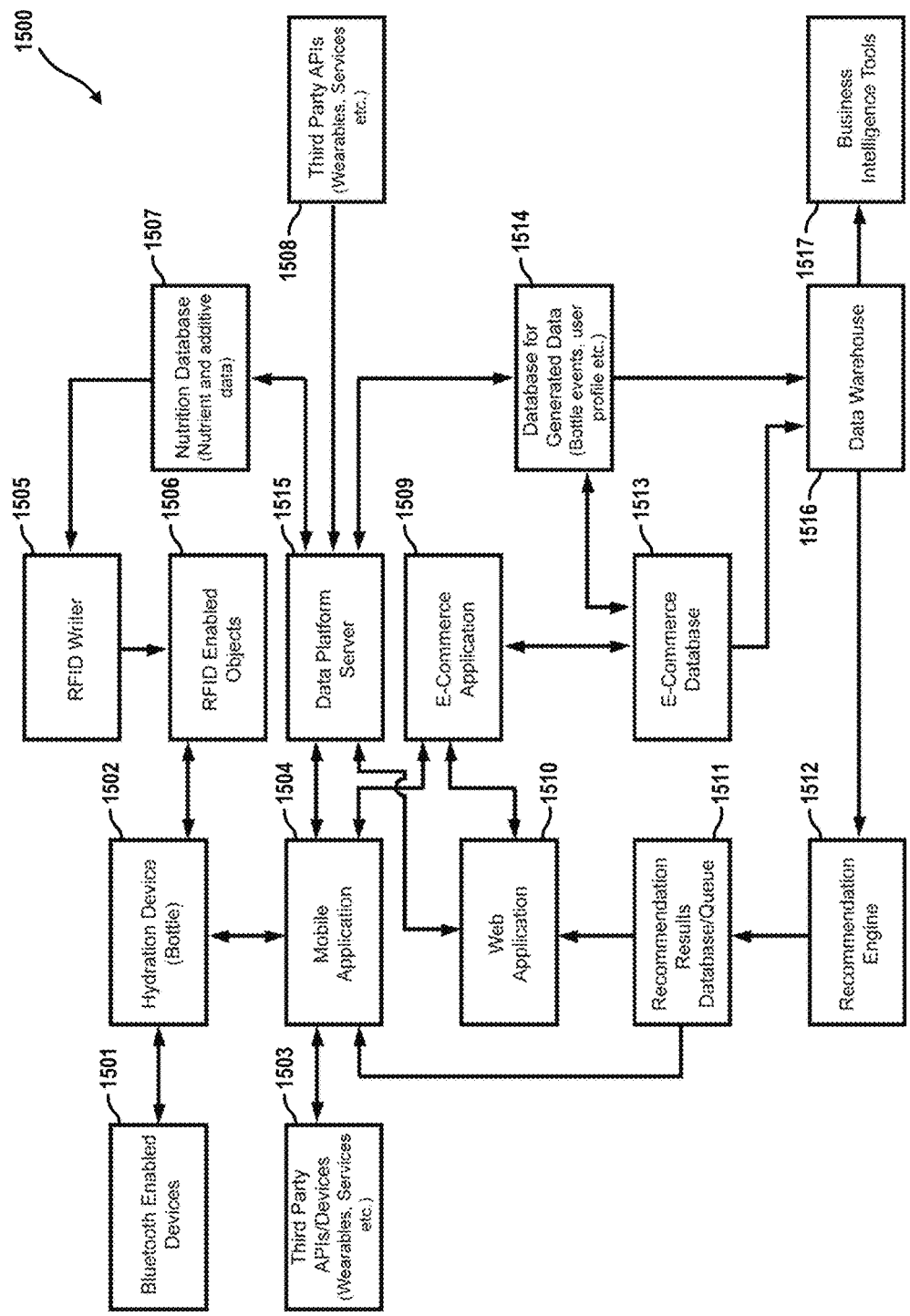
FIG. 15 is a block diagram illustrating example components in a hydration and dispensing system in accordance with one or more embodiments described herein.

FIG. 15 illustrates example components in a hydration and dispensing system 1500 in accordance with one or more embodiments described herein. The hydration device 1502 (e.g., bottle) may communicate with a variety of connected devices. For example, in accordance with at least one embodiment, the hydration device 1502 may communicate with one or more user devices such as Bluetooth enabled user devices 1501 and/or other mobile user devices, which may have various associated mobile applications 1504 installed thereon. Such user devices 1501, 1504 may serve as primary command and control interfaces (e.g., via Bluetooth Low Energy) for controlling various features and functionalities of the hydration device 1502.

In accordance with one or more other embodiments, communications with the hydration device 1502 might involve other wireless and/or radio-based communication standards. For example, additive dispense commands may be transmitted from a user's mobile device 1504 to the hydration device 1502, providing input to trigger a dispensing event within the hydration device 1502. The transmissions between the hydration device 1502 and the user's mobile device 1504 might also communicate hydration data, consumption data, environmental data, and also the exchange of present and/or past (e.g., cached) usage data and/or device data. In accordance with at least one embodiment, the aforementioned examples of relevant data might be further informed, transformed, or modulated in response to information communicated to the hydration device 1502 (e.g., via a mobile application running on the user's device 1504) from third-party APIs and/or devices 1503. For example, information communicated by such third-party APIs and/or devices 1503 may be translated by the mobile application 1504 into dispense commands and/or recommendations that are then transmitted to the hydration device 1502.

The hydration device 1502 communicates with RFID enabled objects 1506, in the preferred embodiment, the communication is with RFID enabled additive vessels whereby an RFID (or similar) tag located on the vessel communicates to the hydration device information relevant to dispensing, nutrition, dosage, and other factors necessary to dispense the additive contained within the vessel with context.

In the preferred embodiment, the hydration device receives additive vessels in a radial formation on the outer circumference of a circle, a centrally located dispensing system then orients an RFID antenna or other wireless communication reader (such as an optical reader) such that it specifically reads and collects data from an additive vessel located at a known index point.

Figure 19:
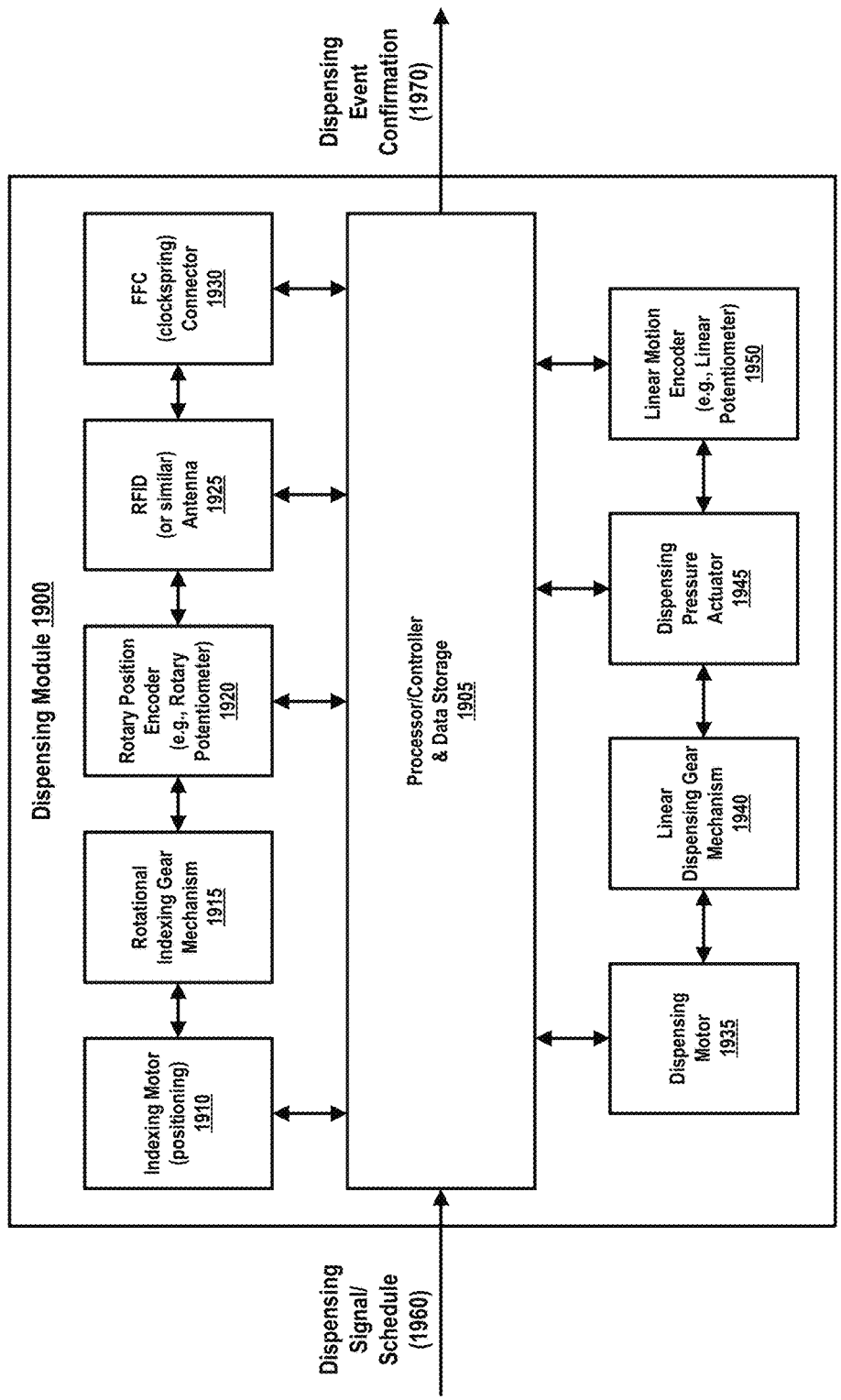
FIG. 19 is a block diagram illustrating example components of a dispensing module in accordance with one or more embodiments described herein.

The aforementioned embodiment is a mechanical system located within the hydration device 1502, and referenced further in FIG. 19. The aforementioned preferred embodiment describes the primary communication process occurring between the hydration device and an RFID enabled object and/or objects. Another embodiment involves the hydration device communicating with objects that provide further context to the device, examples might include context for dispensing actions and/or events, nutrition, user behavior, and hydration, this might be accomplished with the placement of an externally oriented antenna or other form of reader.

In accordance with at least one embodiment described herein, the hydration and dispensing system 1500 includes an RFID writer 1505 that encodes information to an RFID tag or other RFID-enabled object 1506 for the hydration device 1502 to ultimately read and incorporate into further actions. The RFID writer 1505 may be further informed by one or more associated databases such as, for example, a nutrition database 1507 containing relevant information that might include dispensing protocols, nutritional information, and the like.

The hydration device 1502 may communicate with a wireless device 1501, 1504, acting as a command and control interface for the user, and in accordance with at least one embodiment, providing the primary interface to the hydration device 1502. Furthermore, the wireless device may make use of an application 1504 that communicates information to and receives information from the hydration device 1502, while also communicating (e.g., either directly or via a data platform server 1515) with one or more peripheral network systems 1508 (third-party APIs associated with, for example, wearable devices, user services, etc.), 1509 (e-Commerce applications), 1510 (web applications), 1511 (recommendation results databases and/or queues), and 1512 (recommendation engines), which store, share, process, or otherwise handle data relevant to the user experience, dispensing actions, and/or the purchase and/or use of other additive vessels, and the like.

In accordance with at least one embodiment of the present disclosure, more comprehensive data regarding the additive vessels is communicated from, to, and through the mobile application 1504 and/or wireless device. Furthermore, the mobile application 1504 may leverage data from the hydration device 1502 and from one or more other sources, such as, for example, third party APIs 1503 (e.g., "Apple HealthKit", "Fitbit", "MyFitnessPal", etc.) to inform dispensing actions, dispensing recommendations, purchase recommendations, purchase automation, and other prompts to the user or to a third-party user (e.g., a physician or caregiver associated with the user).

Ultimately, all data associated with the system 1500 may be stored and/or processed on every node of the system, to varying extents. In accordance with at least one embodiment, dispensing data may be cached locally on the hydration device 1502 in cases where it is not connected to a peripheral device (such as a mobile phone). Recommendation data, purchase data, nutritional data, and dispensing instructions, may all be stored locally to varying extents on the hydration device 1502 and on the connected wireless device 1501, leveraging the mobile application 1504. It should be understood that the system 1500 is designed such that a portion or multiple portions of the system 1500 can disconnect and remain disconnected for a period of time without eliminating any core elements or features of the user experience, including, for example, additive dispensing and hydration tracking from a portable hydration device.

Figure 16:
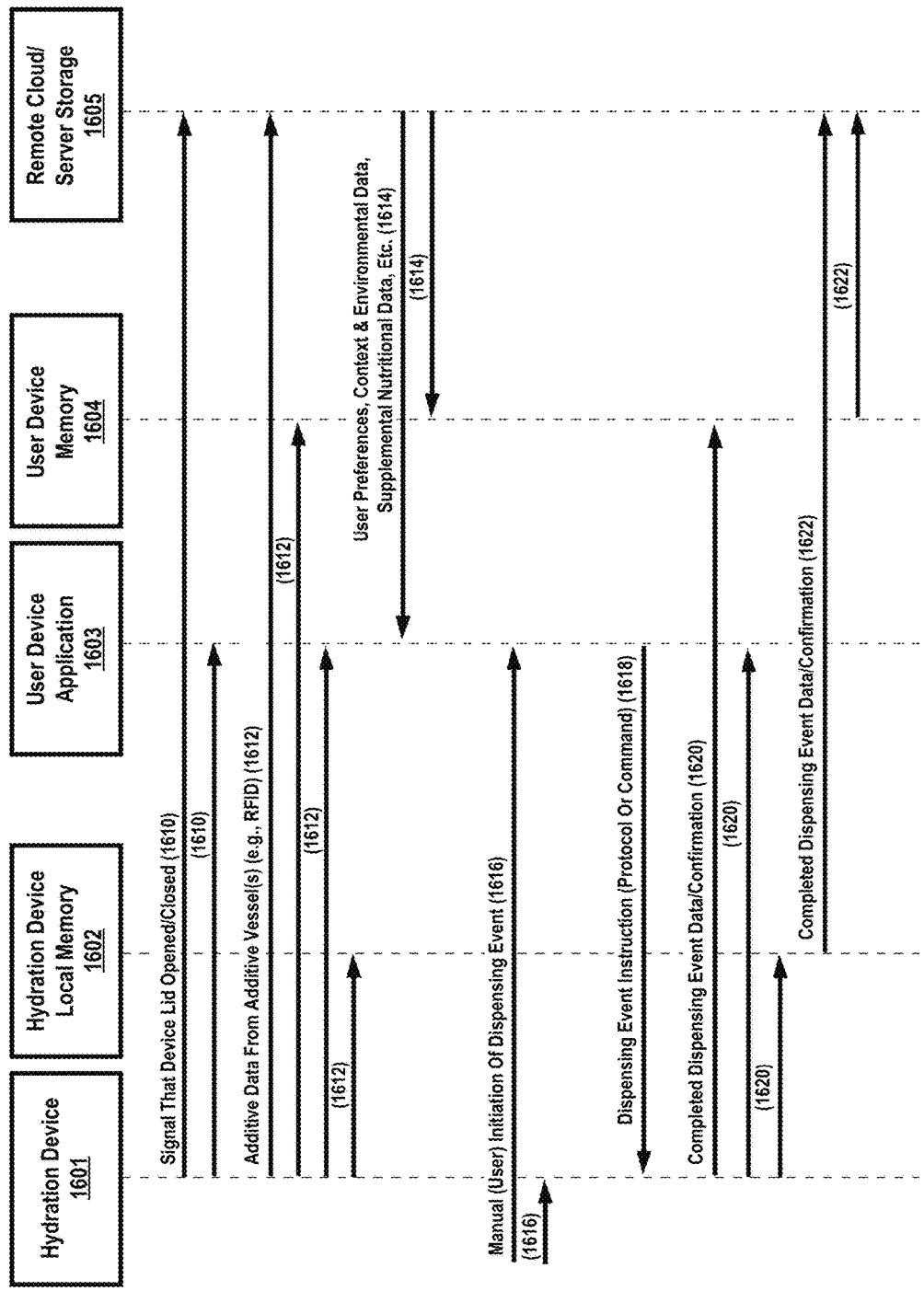
FIG. 16 is a data flow diagram illustrating example data flows between components in a hydration and dispensing system during a dispensing event in accordance with one or more embodiments described herein.

FIG. 16 illustrates example data flows between components in a hydration and dispensing system during a dispensing event in accordance with one or more embodiments described herein. Example data flows are shown between a hydration device 1601, local memory (e.g., storage) of the hydration device 1602, a user device 1603 (e.g., an associated application running on a user device), local memory of the user device 1604, and remote server (e.g., "cloud") storage 1605.

In accordance with at least one embodiment, the data flows illustrated in FIG. 16 (e.g., data flows 1610, 1612, 1614, 1616, 1618, 1620, and 1622) are specific to the scenario where additive vessels have been inserted into the hydration device 1601 and a subsequent dispensing event is to occur. For example, a sensor, in this case a hall-effect switch, informs the device of the lid being opened or closed (1610), in this case the open and close event infers that the user has opened the lid to place additive vessels in the hydration device 1601. The open-close sensor also functions in accordance with at least one embodiment to trigger the dispensing module to orient itself, and therefore the RFID antenna upon a known index point to read data from the additive vessel and subsequently communicate (1612) that data to the device and/or to peripheral devices and/or systems including remote cloud storage and/or servers (1605).

Periodically, user preferences, information, context, data, environmental information, and the like is communicated (1614) from remote storage in the cloud 1605 to the user's mobile device 1603 and to the mobile application, and is stored therein (e.g., in local memory of the user device 1604), subsequently informing the hydration device 1601 via dispensing instructions. A dispensing event can be initiated manually (1616) by the user using the mobile application. Alternatively, the user can initiate a dispensing event more directly (1616) using the interface on the hydration device 1601 itself. In another use case the hydration device 1601 might receive dispensing instructions/protocols (1618) from the mobile device 1603 to instruct the hydration device 1601 to dispense quantities of additive at specific times, following which, confirmation of the dispensing event and data associated with the dispensing event is communicated (1620), (1622) from the hydration device 1601 to the users mobile device 1603 and the storage therein 1604, when a connection to a mobile device is not present, the aforementioned data is stored locally within the hydration device.

Figure 17:
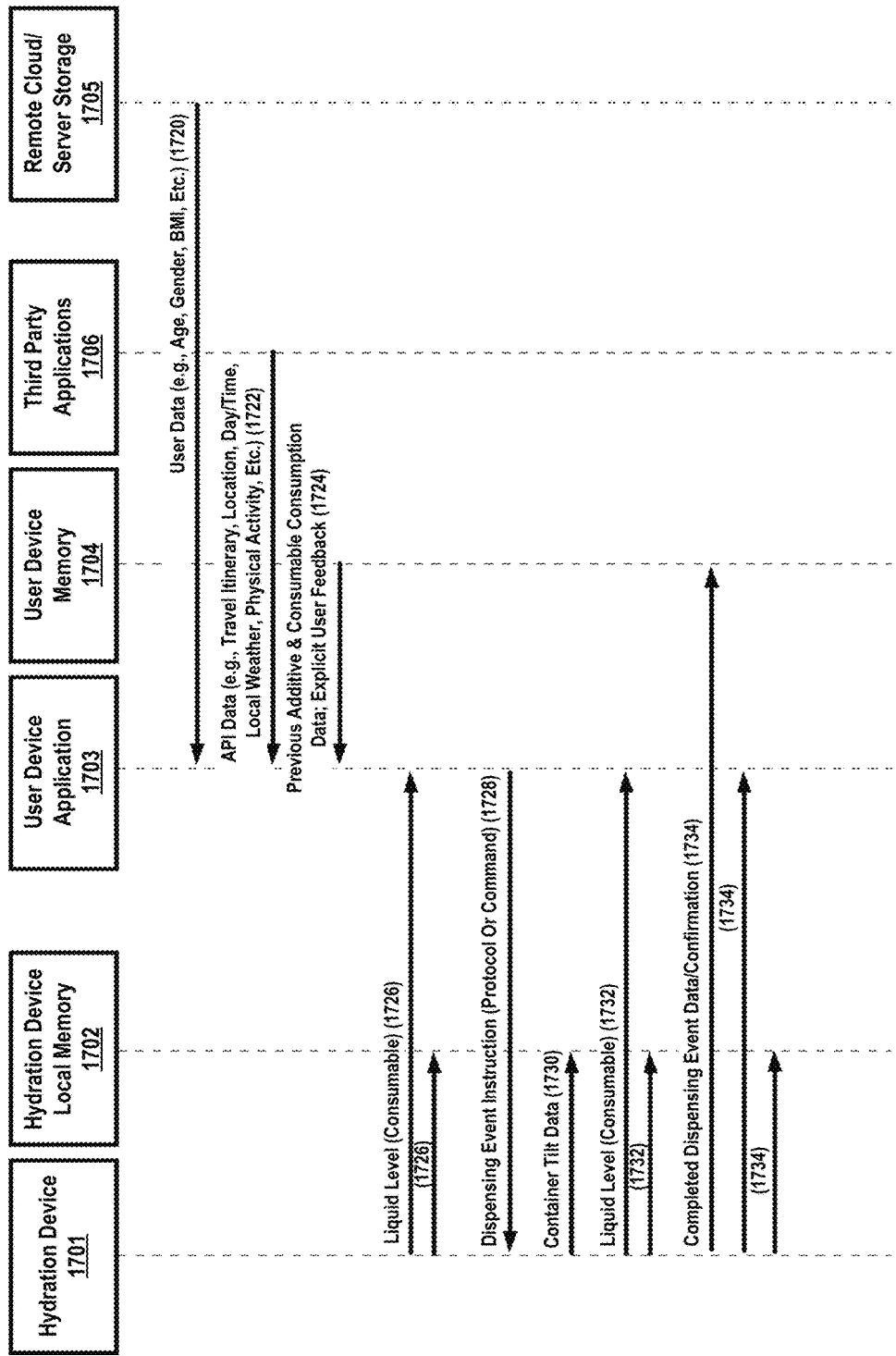
FIG. 17 is a data flow diagram illustrating example data flows between components in a hydration and dispensing system during a dispensing event based on various user, environment, and contextual data in accordance with one or more embodiments described herein.

FIG. 17 illustrates example data flows between components in a hydration and dispensing system during a dispensing event based on various user, environment, and contextual data in accordance with one or more embodiments described herein. In accordance with at least one embodiment, example data flows are shown between a hydration device 1701, local memory (e.g., storage) of the hydration device 1702, a user device 1703 (e.g., an associated application running on a user device), local memory of the user device 1704, remote server (e.g., "cloud") storage 1705, and one or more third-party applications 1706.

In accordance with at least one embodiment, the example data flows illustrated in FIG. 17 (e.g., data flows 1720, 1722, 1724, 1726, 1728, 1730, 1732, and 1734) enable the hydration device 1701 to modify dispensing instructions/protocol more dynamically in response to various data points and/or information relevant to the overall context. In the example shown, there are three sources of data to demonstrate this. Data (1724) that is stored in the mobile device 1703, 1704, data (1722) that is received and/or processed from or by third-party data sources (e.g. APIs) 1706, and data (1720) that is communicated from a remote network and/or cloud server/storage 1705. Data from the aforementioned includes, but is not limited to, user physiological information, demographics, preferences, psychographics, dietary preferences, dietary requirements, nutritional requirements, taste preferences, calendar information, purchase information, physical activity, weather data, location data, geographic information, explicit user feedback, travel information, health information regulatory constraints relevant to dietary and nutritional recommendations and/or dispensing events thereof. The aforementioned data sources might be received and/or processed in real-time, and/or as predictive elements, and/or as historic elements. The liquid level (1726) in the hydration device 1701 is measured prior to a dispensing event, and is communicated to the hydration device 1701 and/or dispensing module, and/or the mobile device 1703 thereby informing the dispensing event preemptively. Following a dispensing event spatial data and/or inertial data, in the preferred embodiment measured and collected by an accelerometer within the hydration device, might initiate and/or inform other functions including but not limited to, level measurement, interface prompts, and data transmission. Following a dispensing event, data confirming a dispensing event (1734) is transmitted, stored, or otherwise processed in a manner previously described herein (e.g., the example data flows shown in FIG. 16 and described above).

Figure 18:
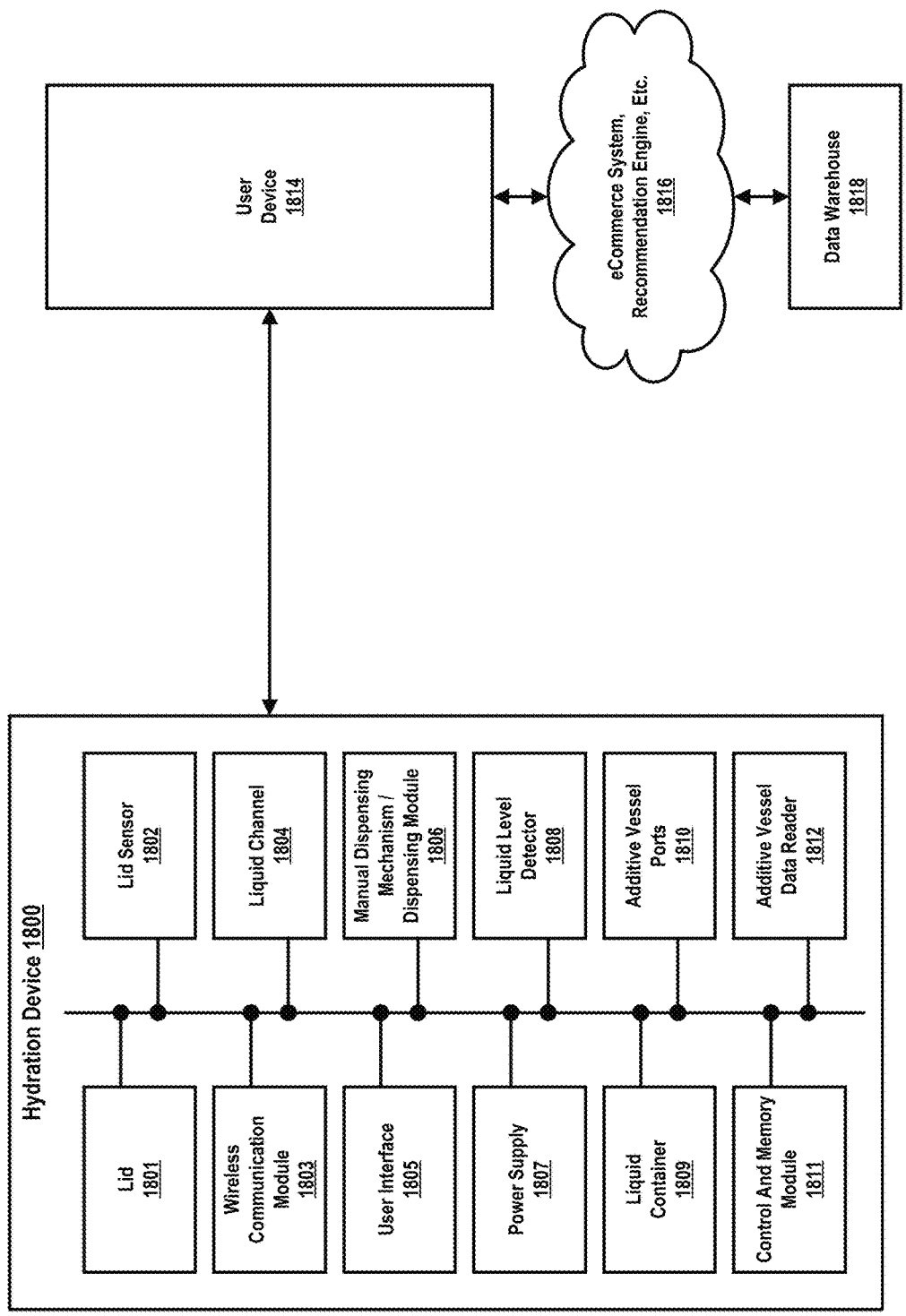
FIG. 18 is a block diagram illustrating example components of a hydration device in accordance with one or more embodiments described herein.

FIG. 18 illustrates example components of a hydration device (e.g., hydration container) 1800 in accordance with one or more embodiments described herein. The hydration device 1800 may include, for example, a lid 1801, one or more lid sensors 1802, a wireless communication module 1803, a liquid channel 1804, a user interface 1805, a manual dispensing mechanism or a dispensing module 1806, a power supply 1807, a liquid level detector 1808, a liquid (e.g., consumable liquid) container 1809, additive vessel ports (e.g., apertures, chambers, etc.) 1810, a control and memory module 1811, and an additive vessel data reader 1812. It should be understood that, in accordance with one or more other embodiments of the present disclosure, the example hydration device 1800 may not include one or more of the components shown in FIG. 18, or may include one or more other components not shown in FIG. 18, where such other components may be included in the hydration device 1800 in addition to or instead of one or more of the example components illustrated.

The hydration device 1800 may be in communication with a user device 1814 via, for example, a wired or wireless connection, and such communication may be on a persistent or periodic/intermittent basis. In accordance with at least one embodiment of the present disclosure, the user device 1814 may act as a proxy through which the hydration device 1800 can exchange (e.g., send and/or receive) data with, for example, an eCommerce system and/or recommendation engine 1816, as well as one or more data warehouses (e.g., storage systems or servers, which may be local or remote, and which may function as a central storage location for a wide range of data associated with the hydration device 1800 and/or a user of the device). The eCommerce system and/or recommendation engine 1816 may provide to the hydration device 1800 (e.g., via the user device 1814), for example, recommendations, contextual modifications, purchase of additive vessels, and the like, related to the hydration device 1800 and overall system.

The lid 1801 (e.g., lid assembly) may be for sealing the system or otherwise connecting a dispensing module and/or additive vessels to the hydration container 1800. In accordance with at least one embodiment, the lid sensor 1802 may be, for example, a hall-effect switch, that informs (e.g., sends an indication to) the hydration device 1800 and the overall system and peripheral network of an event, such as where the lid 1801, or a subassembly of the lid 1801 is removed, replaced, or otherwise moved (e.g., by the user).

In accordance with at least one embodiment, this indication from the lid sensor 1802 signals the dispensing module 1806 and/or additive vessel data reader 1812 to initiate an indexing sequence to read data from the additive vessels (and/or data tags affixed thereon), which may be removably secured in (e.g., held in place within, received in, etc.) the additive vessel ports 1810, and to communicate that data to the hydration system and/or to other components of the overall system. A wireless communication module (e.g., a Bluetooth system or component) 1803 provides a communication mechanism for the hydration device 1800 and/or dispensing module 1806 to transmit and/or receive information to or from other devices.

The liquid channel 1804, which in accordance with at least one embodiment, may be a sealable passage for the consumable liquid contained or retained in the liquid container 1809 of the hydration device 1800 to be consumed by the user without necessarily coming into contact with any of the other system components. The hydration device 1800 may also include a user interface 1805 that enables the user to interact with or otherwise control or interface with the hydration device 1800. For example, in accordance with at least one embodiment, the user interface 1805 may include a display screen (e.g., touch display) and button interface on the hydration device 1800. In accordance with one or more other embodiments, the user interface 1805 may include one or more buttonless interfaces, symbolic interfaces leveraging LEDs, and/or the like.

The hydration device 1800 may include a dispensing module 1806, various features of which are described in greater detail below and illustrated in FIG. 19. In accordance with at least one embodiment of the present disclosure, in place of the dispensing module illustrated in FIG. 19, the hydration device 1800 may include a manual dispensing mechanism 1806 or one or more alternative mechanical solutions that are similar in function to such a manual dispensing mechanism.

Power supply 1807 may be adapted to provide energy to the hydration device 1800, the overall hydration system, and/or subcomponents of the hydration system. The liquid level detector 1808 may be a mechanism by which the hydration device 1800 measures, reads, or otherwise obtains information pertaining to the volume of liquid (e.g., liquid consumable) contained in the liquid container 1809 of the hydration device 1800. In accordance with at least one embodiment, the liquid container 1809 may serve as a receptacle container into which additive vessels dispense additives directly or indirectly for user consumption or use. The additive vessel ports 1810 may receive additive vessels placed or inserted therein by a user such that the additive vessels are able to interface with various other components of the hydration device 1800 such as, for example, the dispensing module 1806, the additive vessel data reader, etc.

The control and memory module (e.g., system) 1811 within the hydration device 1800 may be a mechanism through which the hydration device 1800 can obtain data from the additive vessel or vessels interfacing with the additive vessel ports 1810 or any other subcomponent of the hydration device 1800.

FIG. 19 illustrates example components of a dispensing module 1900 in accordance with one or more embodiments described herein. The dispensing module 1900 may include, for example, a processor/controller 1905 (which may include one or more data storage devices/components), an indexing motor (e.g., positioning motor) 1910, a rotational indexing gear mechanism 1915, a rotary encoder (e.g., a rotary potentiometer) 1920, one or more RFID or similar type antennas 1925, an FFC (clockspring) connector 1930, a dispensing motor 1935, a linear dispensing gear mechanism 1940, one or more dispensing pressure actuators 1945, and a linear motion encoder (e.g., linear potentiometer) 1950. The dispensing module 1900 may receive as input, for example, a dispensing signal or schedule (1960), and generate as output a dispensing event confirmation (1970).

It should be understood that, in accordance with one or more other embodiments of the present disclosure, the example dispensing module 1900 may not include one or more of the components shown in FIG. 19, or may include one or more other components not shown in FIG. 19, where such other components may be included in the dispensing module 1900 in addition to or instead of one or more of the example components illustrated.

The example dispensing module 1900 illustrated in FIG. 19 references a mechanism whereby a subsystem orients the dispensing module 1900 upon a specific location, in this case, a pre-determined, pre-programmed location of an additive vessel. In accordance with one or more embodiments, the dispensing module 1900 may include or utilize a mechanism whereby a subsystem provides input force to an additive vessel to generate a controlled and repeatable dispensing event with completely variable quantities of additives dispensed. Position sensors may act with both the orientation mechanism and the dispensing mechanism to provide a feedback loop for both systems to function with precision, while also delivering relevant data to the device itself (e.g., hydration device, such as the example hydration device 1800 shown in FIG. 18). The indexing motor 1910 and rotational indexing gear mechanism 1915 allow for reliable axial motion of the dispensing module 1900. The RFID antenna (or other similar data reader device) may orient itself with the dispensing module 1900, thereby providing confirmation of positional accuracy, indexing of the additive vessels, and data transmission related to the additive vessels. The dispensing module 1900 receives instructions/protocol (1960) to dispense a specific additive, where such instructions/protocol may include, but are not limited to, a specific time for the dispense event, a quantity of additive to be dispensed, and/or a frequency for dispensing the additive. The dispensing module 1900 may output data (1970) that confirms a successful dispensing event or indicates full or partial failure thereof.

In accordance with at least one embodiment of the present disclosure, the hydration and dispensing system described herein may be implemented in a water bottle or other portable hydration device including, among other components, a user interface screen that is a part of the apparatus itself or is an accessory component thereof. In such an embodiment, the user interface screen may be in communication with both internal software for the device itself, as well as wirelessly communicating to a secondary device fetching and delivering other relevant data.

The foregoing detailed description has set forth various embodiments of the systems, devices, and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Thus, particular embodiments of the subject matter have been described. In some cases, the actions described in accordance with one or more of the embodiments may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A portable container for retaining a liquid, the portable container comprising:
   a hydration container;
   an additive vessel containing an additive;
   an actuator assembly; and
   a dispensing module mounted to and removably secured to the hydration container, the dispensing module including at least one aperture, and the at least one aperture including a first aperture;
   the first aperture receives the additive vessel containing the additive to be dispensed into the liquid;

the actuator assembly dispenses variable quantities of the additive contained in the additive vessel that is received in the first aperture;

the dispenses, performed by the actuator assembly, performed based on data associated with the portable container;

the actuator assembly supported, within the portable container, adjacent the additive vessel; and wherein the portable container includes at least one processor configured to adaptively control the actuator assembly to dispense the variable quantities of the additive based on the data associated with the portable container.

2. The portable container of claim 1, wherein the at least one processor is configured to:

control timing of dispensing of the additive from the additive vessel into the liquid;

control an amount of pressure applied to the additive vessel by the actuator assembly; and control duration of the application of pressure.

3. The portable container of claim 1, the data associated with the device is constituted by use data, the use data associated with use of the portable container and wherein the at least one processor is configured to:

collect the use data associated with use of the portable container; and adjust the dispensing of the additive based on the collected use data, wherein the collected use data includes one or more selected from the group consisting of: an amount of the liquid retained in the portable container; a physical characteristic of the additive to be dispensed; a consumption activity associated with the user of the portable container; a preference of the user of the portable container; and a context of use of the portable container by the user.

4. The portable container of claim 3, wherein the at least one processor is configured to:

transmit the collected use data from the portable container to a remote server in communication with the portable container via a communications network, to a user device associated with the user of the portable container, or both.

5. The portable container of claim 4, wherein the at least one processor is configured to:

receive at the portable container from the server, from the user device, or from both the server and user device, one or more recommendations for the user of the portable container, wherein the one or more recommendations are based on the collected data transmitted from the portable container; and provide the one or more recommendations to the user of the portable container.

6. The portable container of claim 5, wherein the one or more recommendations provided to the user include a recommendation about one or more additives to be purchased for future dispensing by the portable container.

7. The portable container of claim 6, wherein the recommendation about one or more additives to be purchased for future dispensing is based on at least one selected from the group consisting of:

quantities and dates of previous additive purchases by the user;

rate of dispensing of additives into the portable container of the user; and rate of consumption of the liquid retained in the portable container of the user.

8. The portable container of claim 1, further comprising:

a pressure applicator within the actuator assembly;

wherein the pressure applicator is moveable into a position adjacent to a surface of the additive vessel received in the first aperture; and wherein the pressure applicator is configured to apply pressure to the surface of the additive vessel to at least partially release the additive contained in the additive vessel.

9. The portable container of claim 1, wherein the at least one processor is configured to:

monitor an amount of the liquid retained in the portable container;

determine a type of the liquid retained in the portable container;

monitor a rate of consumption of the liquid retained in the portable container; and detect when the amount of the liquid retained in the portable container has increased or decreased.

10. The portable container of claim 9, wherein the at least one processor is configured to:

process sensor data about the amount, type, and/or rate of consumption of the liquid retained in the portable container;

store the sensor data about the amount, type, and/or rate of consumption of the liquid retained in the portable container;

communicate the sensor data about the amount, type, and/or rate of consumption of the liquid retained in the portable container over a communication network; and receive data indicating a recommended amount, a recommended type, and/or a recommended rate of consumption of the liquid retained in the portable container.

11. The portable container of claim 10, wherein the at least one processor is configured to:

present, to the user of the portable container, the received data indicating the recommended amount, the recommended type, and/or the recommended rate of consumption of the liquid retained in the portable container.

12. The portable container of claim 1, wherein the additive vessel received in the first aperture of the portable container includes:

a form factor enabling the additive vessel to recover shape after a dispensing event;

a dispensing valve permitting the dispensing of variable quantities of the additive contained in the additive vessel into the liquid; and a valve mechanism enabling the additive vessel to be removed from the actuator assembly and stored, replaced, or transferred to a second actuator assembly.

13. The portable container of claim 1, further including a lid, the lid received upon the hydration container, and the lid enclosing the additive vessel containing the additive, the actuator assembly, and the dispensing module.

14. The portable container of claim 13, the actuator assembly supported, at least in part, by the lid.

15. The portable container of claim 14, the lid disposed at an open end of the hydration container, and the lid serving to enclose an interior of the hydration container.

16. The portable container of claim 1, further including a drinking channel, the drinking channel providing a channel whereby a user may consume the liquid with the additive in conjunction with holding the portable container.

17. The portable container of claim 16, further including a lid, the lid received upon the hydration container, and the lid enclosing the additive vessel containing the additive, the actuator assembly, and the dispensing module, and the lid including a lid aperture, and the drinking channel passing through the lid aperture.

\* \* \* \* \*